US009005897B2

(12) United States Patent
Lim et al.

(10) Patent No.: US 9,005,897 B2
(45) Date of Patent: Apr. 14, 2015

(54) METHOD OF DERIVING PROGENITOR CELL LINE

(71) Applicant: Agency for Science, Technology and Research, Singapore (SG)

(72) Inventors: Sai Kiang Lim, Singapore (SG); Elias Lye, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 13/788,627

(22) Filed: Mar. 7, 2013

(65) Prior Publication Data
US 2013/0280719 A1 Oct. 24, 2013

Related U.S. Application Data

(60) Division of application No. 12/888,724, filed on Sep. 23, 2010, now abandoned, which is a continuation of application No. 12/065,549, filed as application No. PCT/SG2006/000233 on Aug. 15, 2006, now abandoned.

(60) Provisional application No. 60/713,992, filed on Sep. 2, 2005.

(51) Int. Cl.
C12Q 1/68 (2006.01)
C12N 5/071 (2010.01)
G01N 33/50 (2006.01)
C12N 5/0775 (2010.01)

(52) U.S. Cl.
CPC .......... *G01N 33/5044* (2013.01); *C12N 5/0662* (2013.01); *C12Q 1/6809* (2013.01); *C12N 2501/115* (2013.01); *C12N 2501/135* (2013.01); *C12N 2506/02* (2013.01)

(58) Field of Classification Search
CPC ................ G01N 33/5044; C12N 2501/135; C12N 2501/115; C12N 2506/02; C12N 5/0662; C12Q 1/6809
USPC ................................................ 435/6.13, 366
See application file for complete search history.

(56) References Cited

U.S. PATENT DOCUMENTS

| | | | |
|---|---|---|---|
| 6,355,239 | B1 | 3/2002 | Bruder et al. |
| 7,592,176 | B2 | 9/2009 | Pike et al. |
| 2002/0164308 | A1 | 11/2002 | Reubinoff et al. |
| 2003/0021771 | A1* | 1/2003 | Xu et al. ............ 424/93.21 |
| 2003/0036194 | A1 | 2/2003 | Xu et al. |
| 2004/0052771 | A1 | 3/2004 | Lim |
| 2005/0148034 | A1 | 7/2005 | Hariri et al. |
| 2005/0208029 | A1 | 9/2005 | Umezawa et al. |

FOREIGN PATENT DOCUMENTS

WO WO-01/88104 11/2001

OTHER PUBLICATIONS

Stenderup et al., Bone, 33: 919-926, 2003.*
Balconi G et al. Development of endothelial cell lines from embryonic stem cells: A tool for studying genetically manipulated endothelial cells in vitro. Arterioscler Thromb Vasc Biol. Jun. 2000;20(6):1443-51.
Barberi et al., "Derivation of multipotent mesenchymal precursors from human embryonic stem cells," PLOS Medicine, vol. 2, pp. 554-560 (Jun. 28, 2005).
Barry et al., (2001) Chondrogenic Differentiation of Mesechymal Stem Cells from Bone Marrow: Differentiation-Dependent Gene Expression of Matrix Components. Experimental Cell Research, 268, pp. 189-299. (XP001183120).
Chen Shao-Liang, et al., (2004) Effect on Left Ventricular Function of Intracoronary Transplantation of Autologous Bone Marrow Mesechymal Stem Cell in Patients With Acute Myocardial Infraction, American Journal of Cardiology, vol. 94 (1), pp. 92-95. (XP0009075540).
International Search Report mailed on Nov. 13, 2006, for International Application No. PCT/SG2006/000233 filed Aug. 15, 2006, 4 pages.
Keller, "Embryonic stem cell differentiation: emergence of a new era in biology and medicine," Genes and development, vol. 19, pp. 1129-1155 (May 2005).
Kinnaird, T., et al. (2004), Local Delivery of Marrow-Derived Stromal Cells Augments Collateral Perfusion Through Pracrine Mechanism, Printed from circ.ahajournals.org at European Patent Office on Nov. 27, 2006.
Kliminskaya, L. et al., (2005), Human Embryonic Stem Cells Derived Without Feeder Cells, The Lancet, vol. 365 (9471), pp. 1636-1641. (XP004882308).
Pesce M and Schöler HR. Oct. 4: gatekeeper in the beginnings of mammalian development. Stem Cells. 2001;19(4):271-8.
Pitienger, M.F., et al., (1999), Multi Lineage Potential of Adult Human Mesenchymal Stem Cells, Science, vol. 284 (5411) pp. 143-147. (XP000867221).
Reubinoff et al., "Embryonic stem cell lines from human blastocysts: Somatic differentiation in vitro," Nature Biotechnology, Nature Pub, vol. 18, pp. 399-404 (Apr. 2000).
Schuldiner et al., "effects of eight growth factors on the differentiation of cells derived from human embryonic stem cells," Proceedings of the National Academy of Sciences of USA, vol. 97, pp. 11307-11312 (Oct. 10, 2000).
Wobus et al., "Embryonic stem cells: Prospects for developmental biology and cell therapy," Physiological reviews, vol. 85, pp. 635-678 (Apr. 2005).
Xaymardan, et al. (2004), Platelet-Derived Growth Factor—As Promotes the Generation of Adult Bone Marrow-Derived Cardiac Myocytes. Circulation Research, vol. (94), pp. 39-45.
Yin et al., "Embryonic cell lines with endothelial potential: An in vitro system for studying endothelial differentiation," Arteriosclerosis thrombosis and vascular biology, vol. 24, pp. 691-696 (Apr. 2004).

* cited by examiner

*Primary Examiner* — Thaian N Ton
(74) *Attorney, Agent, or Firm* — Grimes & Yvon LLP

(57) ABSTRACT

We disclose a method comprising: (a) providing an embryonic stem (ES) cell; and (b) establishing a progenitor cell line from the embryonic stem cell; in which the progenitor cell line is selected based on its ability to self-renew. Preferably, the method selects against somatic cells based on their inability to self-renew. Preferably, the progenitor cell line is derived or established in the absence of co-culture, preferably in the absence of feeder cells, which preferably selects against embryonic stem cells. Optionally, the method comprises (d) deriving a differentiated cell from the progenitor cell line.

14 Claims, 27 Drawing Sheets

FIGURE 1E

| e | P3 | P13 |
|---|---|---|
| E-RoSH2.1 | 39.1± 0.65 | 40.1 ± 0.43 |
| E-RoSH3.2 | 39.7± 0.35 | 39.9 ± 0.38 | vWF

Hematoxylin e 
ESC

E-RoSH

FIGURE 4F

| | HUES9.E1 P4 | HUES9.E1 P8 |
|---|---|---|
| f No of metaphase cells analysed | 25 | 28 |
| Chromosome Number: | 46, XX | 46, XX |
| Numerical aberrations | Nil | Nil |
| Structural aberrations: | inv (9) (p11q12) | inv (9) (p11q12) |
| Karyotype: | 46, XX, inv(9) (p11q12) | 46, XX, inv(9) (p11q12) | h Adipogenesis

METHOD OF DERIVING PROGENITOR CELL LINE

This application is a divisional of pending U.S. patent application Ser. No. 12/888,724, filed on Sep. 23, 2010, which is a continuation of abandoned U.S. patent application Ser. No. 12/065,549, filed on Mar. 3, 2008, which is a national stage entry of PCT Application No. PCT/SG2006/000233, filed on Aug. 15, 2006, which claims priority to U.S. provisional application Ser. No. 60/713,992, filed on Sep. 2, 2005.

The foregoing application, and each document cited or referenced in each of the present and foregoing applications, including during the prosecution of each of the foregoing application ("application and article cited documents"), and any manufacturer's instructions or catalogues for any products cited or mentioned in each of the foregoing application and articles and in any of the application and article cited documents, are hereby incorporated herein by reference. Furthermore, all documents cited in this text, and all documents cited or reference in documents cited in this text, and any manufacturer's instructions or catalogues for any products cited or mentioned in this text or in any document hereby incorporated into this text, are hereby incorporated herein by reference. Documents incorporated by reference into this text or any teachings therein may be used in the practice of this invention. Documents incorporated by reference into this text are not admitted to be prior art.

FIELD

The present invention relates to the fields of development, cell biology, molecular biology and genetics. More particularly, the invention relates to a method of deriving progenitor cells from embryonic stem cells.

BACKGROUND

Stem cells, unlike differentiated cells have the capacity to divide and either self-renew or differentiate into phenotypically and functionally different daughter cells (Keller, Genes Dev. 2005; 19:1129-1155; Wobus and Boheler, Physiol Rev. 2005; 85:635-678; Wiles, Methods in Enzymology. 1993; 225:900-918; Choi et al, Methods Mol Med. 2005; 105:359-368).

The pluripotency of mouse embryonic stem cells (ESCs) and their ability to differentiate into cells from all three germ layers makes embryonic stem cells an ideal source of cells for regenerative therapy for many diseases and tissue injuries (Keller, Genes Dev. 2005; 19:1129-1155; Wobus and Boheler, Physiol Rev. 2005; 85:635-678), However, this very property of embryonic stem cells also poses a unique challenge, i.e. generating the appropriate cell types for the treatment of a specific diseased or injured tissue in sufficient quantity and homogeneity to ensure therapeutic efficacy, and inhibiting the generation of other cell types that may have a deleterious effect on the tissue repair and regeneration. At present, protocols that either enhance differentiation of embryonic stem cells towards specific lineages and/or enrich for specific tissue cell types are too inefficient and generally yield heterogeneous cell populations that might be tumorigenic (Keller, Genes Dev, 2005; 19:1129-1155; Wobus and Boheler, Physiol Rev. 2005; 85:635-678).

This invention seeks to solve this and other problems with methods in the art.

SUMMARY

According to $1^{st}$ aspect of the present invention, we provide a method comprising: (a) providing an embryonic stem (ES) cell; and (b) establishing a progenitor cell line from the embryonic stem cell; in which the progenitor cell line is selected based on its ability to self-renew.

Preferably, the method selects against somatic cells based on their inability to self-renew.

In a preferred embodiment, the progenitor cell line is derived or established in the absence of co-culture, preferably in the absence of feeder cells. Preferably, the absence of co-culture selects against embryonic stem cells.

In preferred embodiments, the progenitor cell line is established without transformation. Preferably, the progenitor cell line is established by exposing embryonic stem cells or their descendants to conditions which promote self-renewal of putative progenitor cells. Preferably, the self-renewal-promoting conditions discourage the propagation of embryonic stem cells.

Preferably, the self-renewal-promoting conditions comprise growth in rich media. More preferably, the self-renewal-promoting conditions comprise growing cells in the absence of LIF.

Preferably, the self-renewal-promoting conditions comprise serial passages. Preferably, the self-renewal promoting conditions comprise at least 12 serial passages.

In preferred embodiments, the progenitor cell line has reduced potential compared to the embryonic stem cell. Preferably, the progenitor cell line is lineage restricted, preferably non-pluripotent. Preferably, the progenitor cell line is non-tumorigenic.

Preferably, the step of deriving the progenitor cell line comprises a step of exposing the embryonic stem cell to conditions that enhance differentiation to a specific lineage. Preferably, the differentiation enhancing-conditions comprises generating an embryoid body from the embryonic stem cell. Preferably, the cells are removed from differentiation enhancing-conditions after pluripotency is lost.

Preferably, the removing of the cells from lineage restriction-promoting conditions comprises disaggregating an embryoid body. Preferably, the method comprises disaggregating embryoid bodies which have been grown from between about 3 to 6 days.

In preferred embodiments, the progenitor cell line displays reduced expression of or does not substantially express either or both of OCT4 and alkaline phosphatase activity.

Preferably, the progenitor cell line displays reduced expression of a pluripotency marker compared to an embryonic stem cell from which it is derived, the pluripotency marker preferably selected from the group consisting of: Nanog, BMP4, FGF5, Oct4, Sox-2 and Utf1.

In preferred embodiments, the progenitor cell lines display one or more of the following characteristics: (a) are maintainable in cell culture for greater than 40 generations; (b) have a substantially stable karyotype or chromosome number when maintained in cell culture for at least 10 generations; (c) have a substantially stable gene expression pattern from generation to generation.

Preferably, the progenitor cell line does not substantially induce formation of teratoma when transplanted to a recipient animal, preferably an immune compromised recipient animal, preferably after 3 weeks, more preferably after 2 to 9 months.

Preferably, the embryonic stem cell or progenitor cell line is a mammalian, preferably mouse or human, embryonic stem cell or progenitor cell line.

Preferably, the progenitor cell line comprises an endothelial progenitor cell line, preferably a E-RoSH cell line. Alternatively, or in addition, the progenitor cell line may comprise a mesenchymal progenitor cell line, preferably a huES9.E1 cell line.

In some embodiments, the method further comprises the step of (d) deriving a differentiated cell from the progenitor cell line.

Preferably, the progenitor cell line is propagated for at least 5 generations prior to differentiation.

There is provided, according to a $2^{nd}$ aspect of the present invention, a method according to the $1^{st}$ aspect of the invention for generating a differentiated cell from an embryonic stem (ES) cell.

Preferably, the differentiated cell is an endothelial cell or a mesenchymal cell. More preferably, the differentiated cell is an adipocyte or an osteocyte.

We provide, according to a $3^{rd}$ aspect of the present invention, a method according to the $1^{st}$ or $2^{nd}$ aspect of the invention for up-regulating expression of mesenchymal or endothelial markers of a cell.

As a $4^{th}$ aspect of the present invention, there is provided a method according to the $1^{st}$ or $2^{nd}$ aspect of the invention for down-regulating expression of stem cell or pluripotency markers of a cell.

We provide, according to a $5^{th}$ aspect of the present invention, a method of identifying an agent capable of promoting or retarding self-renewal or differentiation of a stem cell, the method comprising performing a method according to any preceding aspect of the invention in the presence of a candidate molecule, and determining an effect thereon.

The present invention, in a $6^{th}$ aspect, provides a method according to any preceding aspect of the invention for the production of a progenitor cell line or a differentiated cell for the treatment of, or the preparation of a pharmaceutical composition for the treatment of, any one of the following: a disease treatable by regenerative therapy, cardiac failure, bone marrow disease, skin disease, burns, degenerative disease such as diabetes, Alzheimer's disease, Parkinson's disease and cancer.

In a $7^{th}$ aspect of the present invention, there is provided a progenitor cell line produced by a method according to any preceding aspect of the invention.

According to an $8^{th}$ aspect of the present invention, we provide a differentiated cell produced by a method according to any preceding aspect of the invention.

We provide, according to a $9^{th}$ aspect of the invention, a method of generating a differentiated cell from an embryonic stem (ES) cell, the method comprising: (a) deriving a progenitor cell line from the embryonic stem cell; (b) propagating the progenitor cell line; and (c) deriving a differentiated cell from the progenitor cell line.

There is provided, in accordance with a $10^{th}$ aspect of the present invention, a method comprising: (a) providing an embryonic stem (ES) cell; (b) deriving a progenitor cell from the embryonic stem cell; and (c) establishing a progenitor cell line from the progenitor cell, in which progenitor cells are selected based on their ability to self-renew.

BRIEF DESCRIPTION OF THE DRAWINGS

FIG. 1. Derivation of E-RoSH cell lines.

FIG. 1E. Average chromosome number from 20 metaphase nuclei in E-RoSH2.1 and 3.2 lines at passage 3 and 13;

FIG. 2. Relative gene expression analysis by quantitative RT-PCR analysis. The expression level is normalized against that of embryonic stem cells and expressed as a logarithmic function.

FIG. 3. Characterization of E-RoSH cells.

FIG. 4. Characterization of HuES9.E1 cells.

FIG. 4F. Karyotype analysis of HuES9.E1 at passage 4 and passage 8.

DETAILED DESCRIPTION

Figure 1A:
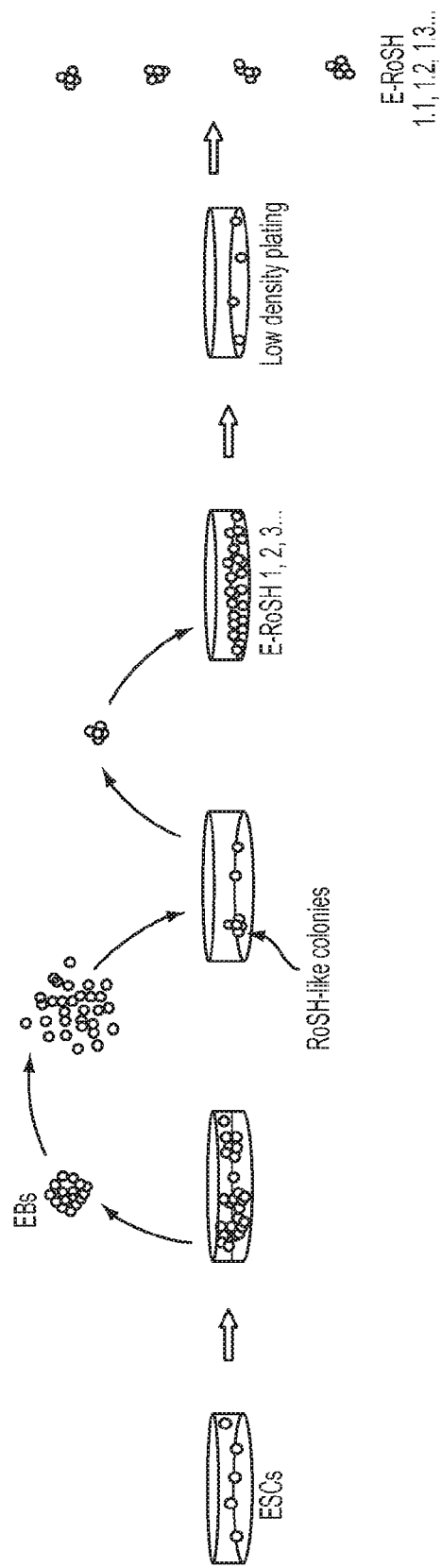
FIG. 1A. Embryonic stem cells are plated singly on methylcellulose based media to form embryoid bodies (EBs). At day 3-6, embryoid bodies are harvested, dissociated by collagenase and cultured as a monolayer on gelatinized feeder plate. RoSH-like colonies with adherent fibroblast-like cells and ring-like structures are selected and propagated on gelatinized plates to generate E-RoSH 1, 2, 3 . . . . Each of the cultures are then plated at a low density of 10-100 cells per 10 cm plate and single RoSH like colonies are picked to established sublines, E-RoSH 2.1, 2.2, 2.3 . . . etc.

We demonstrate that it is possible to derive progenitor cell lines from embryonic stem cells (ES), based on the ability of progenitor cells to self-renew. Unlike terminally differentiating cells, putative progenitor cells with self-renewing properties can be selected and propagated without transformation.

Our methods therefore generally involve deriving progenitor cell lines of limited potential from embryonic stem cells by culturing the pluripotent cells in vitro. This enables the expansion of a progenitor cell with a highly restricted differentiation potential that, upon differentiation, will generate a highly enriched population of a specific cell type with reduced or abolished tumorigenic potential.

We therefore use this property of self-renewal of progenitor cells as the underlying principle of self-selection for generating lineage restricted progenitor cell lines from embryonic stem cells.

Absence of Co-Culture

In preferred embodiments, however, the method further includes culture of cells in conditions that promote growth of progenitor cells, and optionally retard or prevent growth or propagation of embryonic stem cells.

Thus, in highly preferred embodiments, our methods involve culturing putative progenitor cells in the absence of co-culture, as a monolayer or in the absence of feeder cells. The term "co-culture" refers to a mixture of two or more different kinds of cells that are grown together, for example, stromal feeder cells. According to preferred embodiments of the methods described here, the embryonic stem cells are cultured in the absence of feeder cells to establish a progenitor cell line.

Biasing Differentiation

In preferred embodiments, the method for generating embryonic stem cell-derived progenitor cell lines of specific lineages preferably further comprises a first step of biasing differentiation of embryonic stem cells towards a specific desired lineage or lineage of interest. Our methods may also comprise a second step of encouraging self-renewal of putative progenitor cells and discouraging the propagation of embryonic stem cells.

The first step may comprise promoting the growth or propagation of a specific lineage of interest. Different progenitor cell lines of specific lineages of interest may be made by exposing the cells to conditions that promote the differentiation of those lineages of interest. For example, the embryonic stem cells may be exposed to growth factors or small molecules such as ligands that promote or enable differentiation.

Thus, the methods described here for establishing embryonic stem cell-derived cell lines of specific lineages preferably include a step of enhancing differentiation of embryonic stem cells towards that specific lineage. Preferably, the differentiation-enhancing step is carried out for a predetermined period of time. Thus, preferably, the embryonic stem cells or their descendants are transiently exposed to differentiation-enhancing environment.

The choice of the method of enhancing or biasing differentiation will depend on the specific cell lineage of interest for which it is desired to produce progenitor cells. The person skilled in the art will be aware of the various methods which may be used for different cells.

Endodermal Progenitor Cells

Where it is desired to bias differentiation of embryonic stem cells towards endodermal types of tissues, for example, embryoid bodies may be formed and disaggregated (see later). The disaggregated embryoid bodies may be exposed to growth factors or drugs or combinations thereof that induce endodermal differentiation. Examples of such growth factors and drugs include activin A, FGF4, dexamethasone and retinoic acid.

Hematopoietic and Endothelial Progenitor Cells

On the other hand, where it is desired to bias differentiation of embryonic stem cells towards hematopoietic or endothelial lineages, the disaggregated embryoid bodies may be exposed to growth factors or drugs or combinations thereof that induce hematopoietic or endothelial differentiation. Examples of such growth factors and drugs include GM-CSF, G-CSF, SCF, PDGF, IL-3, erythropoietin, thrombopoeittin, TNFα, and rapamycin.

Cardiac Mesoderm and Skeletal Myoblast Progenitor Cells

On the other hand, where it is desired to bias differentiation of embryonic stem cells towards cardiac mesoderm or skeletal myoblast lineages, the disaggregated embryoid bodies may be exposed to growth factors or drugs or combinations thereof that induce cardiac mesoderm or skeletal myoblast differentiation. Examples of such growth factors and drugs include dexamethasone, inhibitors of PPARγ and testosterone or its analogs.

The second step may comprise plating the differentiating cells in a rich media. In such embodiments, continued propagation will selectively enrich for progenitor cells which can then be cloned.

Formation of Embryoid Bodies

In some embodiments, the differentiation-enhancing step comprises formation of embryoid bodies from embryonic stem cells. Embryoid bodies, and methods for making them, are known in the art. The term "embryoid body" refers to spheroid colonies seen in culture produced by the growth of embryonic stem cells in suspension. Embryoid bodies are of mixed cell types, and the distribution and timing of the appearance of specific cell types corresponds to that observed within the embryo. Preferably, the embryoid bodies are generated by plating out embryonic stem cells onto semi-solid media, preferably methylcellulose media as described in Lim et al, Blood. 1997; 90:1291-1299. Preferably, the embryoid bodies are between 3 to 6 days old.

In such embodiments, the embryoid body is disaggregated, i.e., separating the component cells from each other, e.g., by collagenase or trypsin treatment, in order to remove the cells from lineage restriction-promoting conditions.

The method in preferred embodiments comprises a step of choosing a putative progenitor cell for the desired specific lineage. The choosing may be conducted based on morphology of the cell, or by expression or markers, etc. Gene expression profiling or antigen profiling may also be used to choose specific progenitor cells which are of a desired lineage. The chosen putative progenitor cell for the desired specific lineage may then be cultured, or further choosing steps conducted thereon.

In preferred embodiments, the differentiation-enhancing step is followed by exposing differentiating cells to conditions which encourage self-renewal of putative progenitor cells and discourage the propagation of embryonic stem cells. Such conditions may preferably comprise culture in the absence of co-culture or feeder cells (see above).

Rich Media

Alternatively, or in addition, such conditions comprise plating in rich media. The term "rich media" as used in this document is intended to refer to media which is nutrient rich. Preferably, such media comprises essential nutrients required for growth of the relevant cell. Preferably, the rich media contain serum. More preferably, it comprises substantially all the nutrients required for such growth. Most preferably, the rich medium supports, promotes and encourages growth of the relevant cells. in highly preferred embodiments, the relevant cell is a progenitor cell or a putative progenitor cell of interest. An example of a rich medium is DMEM with 4500 mg/l D-glucose, supplemented with 20% fetal calf serum, non essential amino acids, L-glutamine and β-mercaptoethanol.

In preferred embodiments, such rich media does not comprise additional growth regulators or hormones that allow, promote or encourage growth of embryonic stem cells, such as Leukemia inhibitory Factor (LIF).

According to such embodiments, continued propagation will selectively enrich for progenitor cells which can then be cloned.

Long-Term Maintenance in Culture

Preferably, the methods described here involve culturing the embryonic stem cells or their descendants for more than one generation. Preferably, the cells are cultured for more than 5, more than 10, more than 15, more than 20, more than 25, more than 50, more than 40, more than 45, more than 50, more than 100, more than 200, more than 500 or more than 800 generations. In particular, the cell lines may be maintained for 1, 2, 3, 4, 5, 6, 7, 8, 9, 10, 11, 12, 13, 14, 15, 20, 25, 30, 35, 40, 45, 50, 75, 100, 200, 500 or more generations.

Cells in culture will generally continue growing until confluence, when contact inhibition causes cessation of cell division and growth. Such cells may then be dissociated from the substrate or flask, and "split" or passaged, by dilution into tissue culture medium and replating. The progenitor cells may therefore be passaged, or split during culture; preferably they are split at a ratio of 1:2 or more, preferably 1:3, more preferably 1:4, 1:5 or more. The term "passage" designates the process consisting in taking an aliquot of a confluent culture of a cell line, in inoculating into fresh medium, and in culturing the line until confluence or saturation is obtained.

The progenitor cells derived according to the methods described here may however be maintained for a large number of generations, based on their capacity to self-renew. On the other hand, it has been established that "normal" (i.e., untransformed somatic) cells derived directly from an organism are not immortal. In other words, such somatic cells have a limited life span in culture (they are mortal). They will not continue growing indefinitely, but will ultimately lose the ability to proliferate or divide after a certain number of generations. On reaching a "crisis phase" such cells die after about 50 generations. Thus, such somatic cells may only be passaged a limited number of times.

Importantly, the progenitor cells are able to maintain self renewal without the requirement for transformation. Thus, for example, known transformation treatments such as fusion with immortalised cells such as tumour cells or tumour cell lines, viral infection of a cell line with transforming viruses such as SV40, EBV, HBV or HTLV-1, transfection with specially adapted vectors, such as the SV40 vector comprising a sequence of the large T antigen (R. D. Berry et al., Br. J. Cancer, 57, 287-289, 1988), telomerase (Bodnar-A-G. et. al., Science (1998) 279: p. 349-52) or a vector comprising DNA sequences of the human papillomavirus (U.S. Pat. No. 5,376, 542), introduction of a dominant oncogene, or by mutation are therefore not required in the methods described here for making progenitor cell lines.

According to preferred embodiments of the methods described here, progenitor cells may be propagated without transformation for more than 50 generations. In preferred embodiments, the progenitor cells may be propagated indefinitely and without transformation as progenitor cell lines. The progenitor cells and progenitor cell lines are preferably lineage restricted compared to their parental embryonic stem cells. In particular, they are not capable of giving rise to all three germ layers. In highly preferred embodiments, the progenitor cell lines are preferably non-pluripotent.

Characteristics of Progenitor Cells

In preferred embodiments, the progenitor cells and cell lines (or the differentiated cells derived from them) do not display one or more characteristics of embryonic stem cells. Preferred such characteristics include expression of the OCT4 gene and alkaline phosphatase activity. Preferably, the progenitor cell line exhibits reduced expression of one or more characteristic markers of pluripotency. Such pluripotency markers are described in further detail below, but include Nanog, BMP4, FGF5, Oct4, Sox-2 and Utf1.

Progenitor cells made by the methods described here are preferably non-tumorigenic. Preferably, the progenitor cells when implanted into an immune compromised or immunodeficient host animal do not result in tumours, compared to implantation of parental embryonic stem cells which results in tumour formation. Preferably, the immune compromised or immunodeficient host animal is a SCID mouse or a Rag1−/− mouse. Preferably, the progenitor cells do not form tumours after prolonged periods of implantation, preferably greater than 2 weeks, more preferably greater than 2 months, most preferably greater than 9 months. Detailed protocols for tumourigenicity testing are set out in the Examples.

Progenitor cells made by the methods described here are also preferably display one or more of the following characteristics. They have a substantially stable karyotype as assessed by chromosome number, preferably when maintained in cell culture for at least 10 generations. They also preferably display a substantially stable gene expression pattern from generation to generation. By this we mean that the expression levels one or more, preferably substantially all, of a chosen set of genes does not vary significantly between a progenitor cell in one generation and a progenitor cell in the next generation.

Preferably, the set of genes comprises one or more, a subset, or all of, the following: cerberus (GenBank Accession nos: NM_009887, AF031896, AF035579), FABP (GenBank Accession nos: NM_007980, M65034, AY523818, AY523819), Foxa2 (GenBank™. Accession nos: NM_010446, X74937, L10409), Gata-1 (GenBank Accession nos: NM_008089, X15763, BC052653), Gata-4 (GenBank Accession nos: NM_008092, AF179424, U85046, M98339, AB075549), Hesx1 (GenBank Accession nos: NM_010420, X80040, U40720, AK082831), HNF4a (GenBank Accession nos: NM_008261, D29015, BC039220), c-kit (GenBank Accession nos: NM_021099, Y00864, AY536430, BC075716, AK047010, BC026713, BC052457, AK046795), PDGFRα (NM_011058, M57683, M84607, BC053036), Oct4 (GenBank Accession nos: NM_013633, X52437, M34381, BC068268), Runx1 (GenBank Accession nos: NM_009821, D26532, BC069929, AK051758), Sox17 (GenBank Accession nos: NM_011441, D49474, L29085, AK004781), Sox2 (GenBank Accession nos: NM_011443, U31967, AB108673), Brachyury (NM_009309, X51683), TDGF1 (GenBank Accession nos: NM_011562, M87321) and Tie-2 (GenBank Accession nos: NM_013690, X67553, X71426, D13738, BC050824).

The methods described here enable the production of progenitor cells and progenitor cell lines as well as differentiated cells, which comprise clonal descendants of progenitor cells. The term "clonal descendant" of a cell refers to descendants of the cells which have not undergone substantially any transforming treatment or genetic alteration. Such clonal descendants have not undergone substantial genomic changes are substantially genetically identical to the parent cell, or an ancestor, preferably, the embryonic stem cell (save with reduced potency). The term "progenitor cell" should also preferably be taken to include cell lines derived from progenitor cells, i.e., progenitor cell lines, and vice versa.

Regulators of Self-Renewal and Differentiation

Our methods may also be used to identify putative regulators of self-renewal or differentiation. The methods involve conducting the methods described for production of progenitor cell lines or differentiated cells in the presence and absence of a candidate molecule, and identifying if the presence of the molecule has any effect on the process. For example, a molecule which accelerates the production of progenitor cells or differentiated cells may be used as a positive regulator of differentiation (or alternatively as an inhibitor of self-renewal). Conversely, a molecule which retards the process can be considered an inhibitor of differentiation or a promoter of self-renewal.

In preferred embodiments, we also provide a cell, preferably a progenitor, of a selected lineage, obtainable according to the method. Hitherto, preparations of progenitors were too impure for certainty as to whether any chosen cell was a progenitor cell. With culture according to the invention that can give rise to substantially 100% pure preparations of progenitors, isolation of a single progenitor is achieved.

We further provide in preferred embodiments a composition comprising a plurality of cells, wherein a majority of the cells are progenitor cells of a selected lineage. Preferably, at least 60% of the cells axe progenitor cells of the selected lineage. More preferably, at least 60% of the cells are progenitor cells. In addition, the invention provides an isolated progenitor cell. The term cell line preferably refers to cells that can be maintained and grown in culture and display an immortal or indefinite life span.

The methods described here may be combined with decreasing the activity of mTOR to promote differentiation, as described in U.S. 60/609,216, herein incorporated by reference.

Progenitor Cells and Stem Cells

The methods described here are capable of producing progenitor cells, and cell lines thereof.

When embryonic stem cells differentiate, they generally recapitulate the complexity of early mammalian development where embryonic stem cells transit through a series of lineage restriction to generate progenitor cells of decreasing lineage potential before finally generating terminally differentiated cells representing all three germ layers (Wiles, Methods in Enzymology. 1993; 225:900-918). This is exemplified by the process of hematopoiesis, where increasingly lineage-restricted hematopoietic progenitors appearing in a sequential manner similar to that found within the mouse embryo, can be identified within embryoid bodies (Choi et al, Methods Mol Med. 2005; 105:359-368).

Typically, stem cells generate an intermediate cell type or types before they achieve their fully differentiated state, referred to as a precursor or progenitor cell. Progenitor or precursor cells in foetal or adult tissues are partly differentiated cells that divide and give rise to differentiated cells. Such cells are usually regarded as "committed" to differentiating along a particular cellular development pathway, Progenitor cells are therefore sometimes referred to as "committed stem cells".

Our methods are capable of producing of progenitor cells and cell lines of various types.

For example, we disclose a method of making peripheral blood progenitor cells (PBPC), neuronal progenitor cells, haematopoeitic progenitor cells, myeloid progenitor cells, epithelial progenitor cells, bone marrow stromal cells, skeletal muscle progenitor cells, pancreatic islet progenitor cells, mesenchymal progenitor cells, cardiac mesodermal stem cells, lung epithelial progenitor cells, liver progenitors, and endodermal progenitor cells.

Progenitor cells made according to the methods described here can be used for a variety of commercially important research, diagnostic, and therapeutic purposes. These uses are generally well known in the art, but will be described briefly here.

For example, stem cells may be used to generate progenitor cell populations for regenerative therapy. Progenitor cells may be made by ex vivo expansion or directly administered into a patient. They may also be used for the re-population of damaged tissue following trauma.

Thus, hematopoietic progenitor cells may be used for bone marrow replacement, while cardiac progenitor cells may be used for cardiac failure patients. Skin progenitor cells may be employed for growing skin grafts for patients and endothelial progenitor cells for endothelization of artificial prosthetics such as stents or artificial hearts.

Embryonic stem cells and their tissue stem cell derivatives may be used as sources of progenitor cells for the treatment of degenerative diseases such as diabetes, Alzheimer's disease, Parkinson's disease, etc. Stem cells, for example may be used as sources of progenitors for NK or dendritic cells for immunotherapy for cancer, which progenitors may be made by the methods and compositions described here.

It will be evident that the methods and compositions described here enable the production of progenitor cells, which may of course be made to differentiate using methods known in the art. Thus, any uses of differentiated cells will equally attach to those progenitor cells for which they are sources.

Progenitor cells produced by the methods and compositions described here may be used for, or for the preparation of a pharmaceutical composition for, the treatment of a disease. Such disease may comprise a disease treatable by regenerative therapy, including cardiac failure, bone marrow disease, skin disease, burns, degenerative disease such as diabetes, Alzheimer's disease, Parkinson's disease, etc and cancer.

We therefore describe a method of treatment of a disease comprising: (a) providing an embryonic stem (ES) cell; (b) establishing a progenitor cell line from the embryonic stem cell in which the progenitor cell line is selected based on its ability to self-renew; (d) optionally deriving a differentiated cell from the progenitor cell line; and (e) administering the progenitor cell line or the differentiated cell into a patient.

Differentiated Cells

Differentiated cells, such as terminally differentiated cells, may be derived from the progenitor cells or cell lines made according to the methods described. We therefore disclose methods for generating differentiated cells, the methods comprising generating progenitor cells or cell lines as described, and deriving differentiated cells from these.

Differentiated cells which may be made according to the methods described here may include any or all of the following:

i) adipocyte: the functional cell type of fat, or adipose tissue, that is found throughout the body, particularly under the skin. Adipocytes store and synthesize fat for energy, thermal regulation and cushioning against mechanical shock ii) cardiomyocytes: the functional muscle cell type of the heart that allows it to beat continuously and rhythmically iii) chondrocyte: the functional cell type that makes cartilage for joints, ear canals, trachea, epiglottis, larynx, the discs between vertebrae and the ends of ribs iv) fibroblast: a connective or support cell found within most tissues of the body. Fibroblasts provide an instructive support scaffold to help the functional cell types of a specific organ perform correctly.

v) hepatocyte: the functional cell type of the liver that makes enzymes for detoxifying metabolic waste, destroying red blood cells and reclaiming their constituents, and the synthesis of proteins for the blood plasma vi) hematopoietic cell: the functional cell type that makes blood. Hematopoietic cells are found within the bone marrow of adults. In the fetus, hematopoietic cells are found within the liver, spleen, bone marrow and support tissues surrounding the fetus in the womb.

vii) myocyte: the functional cell type of muscles viii) neuron: the functional cell type of the brain that is specialized in conducting impulses ix) osteoblast: the functional cell type responsible for making bone x) islet cell: the functional cell of the pancreas that is responsible for secreting insulin, glucogon, gastrin and somatostatin. Together, these molecules regulate a number of processes including carbohydrate and fat metabolism, blood glucose levels and acid secretions into the stomach.

Uses of Progenitor Cells and Differentiated Cells

Progenitor cell lines and differentiated cells made according to the methods and compositions described here may be used for a variety of commercially important research, diagnostic, and therapeutic purposes.

For example, populations of undifferentiated cells may be used to prepare antibodies and cDNA libraries that are specific for the differentiated phenotype, General techniques used in raising, purifying and modifying antibodies, and their use in immunoassays and immunoisolation methods are described in Handbook of Experimental Immunology (Weir & Blackwell, eds.); Current Protocols in Immunology (Coligan et al., eds.); and Methods of Immunological Analysis (Masseyeff et al., eds., Weinheim: VCH Verlags GmbH). General techniques involved in preparation of mRNA and cDNA libraries are described in RNA Methodologies: A Laboratory Guide for Isolation and Characterization (R. E. Farrell, Academic Press, 1998); cDNA Library Protocols (Cowell & Austin, eds., Humana Press); and Functional Genomics (Hunt & Livesey, eds., 2000). Relatively homogeneous cell populations are particularly suited for use in drug screening and therapeutic applications.

These and other uses of progenitor cell lines and differentiated cells are described in further detail below, and elsewhere in this document. The progenitor cell lines and differentiated cells may in particular be used for the preparation of a pharmaceutical composition for the treatment of disease. Such disease may comprise a disease treatable by regenerative therapy, including cardiac failure, bone marrow disease, skin disease, burns, degenerative disease such as diabetes, Alzheimer's disease, Parkinson's disease, etc and cancer.

Drug Screening

Progenitor cell lines and differentiated cells made according to the methods and compositions described here may also be used to screen for factors (such as solvents, small molecule drugs, peptides, polynucleotides, and the like) or environmental conditions (such as culture conditions or manipulation) that affect the characteristics of differentiated cells.

In some applications, progenitor cell lines and differentiated cells are used to screen factors that promote maturation, or promote proliferation and maintenance of such cells in long-term culture. For example, candidate maturation factors or growth factors are tested by adding them to progenitor cells or differentiated cells in different wells, and then determining any phenotypic change that results, according to desirable criteria for further culture and use of the cells.

Furthermore, gene expression profiling of progenitor cell lines and differentiated cells may be used to identify receptors, transcription factors, and signaling molecules that are unique or highly expressed in these cells. Specific ligands, small molecule inhibitors or activators for the receptors, transcription factors and signaling molecules may be used to modulate differentiation and properties of progenitor cell lines and differentiated cells.

Particular screening applications relate to the testing of pharmaceutical compounds in drug research. The reader is referred generally to the standard textbook "In vitro Methods in Pharmaceutical Research", Academic Press, 1997, and U.S. Pat. No. 5,030,015), as well as the general description of drug screens elsewhere in this document. Assessment of the activity of candidate pharmaceutical compounds generally involves combining the differentiated cells with the candidate compound, determining any change in the morphology, marker phenotype, or metabolic activity of the cells that is attributable to the compound (compared with untreated cells or cells treated with an inert compound), and then correlating the effect of the compound with the observed change.

The screening may be done, for example, either because the compound is designed to have a pharmacological effect on certain cell types, or because a compound designed to have effects elsewhere may have unintended side effects. Two or more drugs can be tested in combination (by combining with the cells either simultaneously or sequentially), to detect possible drug-drug interaction effects. In some applications, compounds are screened initially for potential toxicity (Castell et al., pp. 375-410 in "In vitro Methods in Pharmaceutical Research," Academic Press, 1997). Cytotoxicity can be determined in the first instance by the effect on cell viability, survival, morphology, and expression or release of certain, markers, receptors or enzymes. Effects of a drug on chromosomal DNA can be determined by measuring DNA synthesis or repair. [$^3$H]thymidine or BrdU incorporation, especially at unscheduled times in the cell cycle, or above the level required for cell replication, is consistent with a drug effect. Unwanted effects can also include unusual rates of sister chromatid exchange, determined by metaphase spread. The reader is referred to A. Vickers (PP 375-410 in "In vitro Methods in Pharmaceutical Research," Academic Press, 1997) for further elaboration.

Tissue Regeneration

Progenitor cell lines and differentiated cells made according to the methods and compositions described here may also be used for tissue reconstitution or regeneration in a human patient in need thereof. The cells are administered in a manner that permits them to graft to the intended tissue site and reconstitute or regenerate the functionally deficient area.

For example, the methods and compositions described here may be used to modulate the differentiation of stem cells. Progenitor cell lines and differentiated cells may be used for tissue engineering, such as for the growing of skin grafts. Modulation of stem cell differentiation may be used for the bioengineering of artificial organs or tissues, or for prosthetics, such as stents.

In another example, neural progenitor cells are transplanted directly into parenchymal or intrathecal sites of the central nervous system, according to the disease being treated. Grafts are done using single cell suspension or small aggregates at a density of 25,000-500,000 cells per µL (U.S. Pat. No. 5,968,829). The efficacy of neural cell transplants can be assessed in a rat model for acutely injured spinal, cord as described by McDonald et al. (Nat. Med. 5:1410, 1999. A successful transplant will show transplant-derived cells present in the lesion 2-5 weeks later, differentiated into astrocytes, oligodendrocytes, and/or neurons, and migrating along the cord from the lesioned end, and an improvement in gate, coordination, and weight-bearing.

Certain neural progenitor cells are designed for treatment of acute or chronic damage to the nervous system. For example, excitotoxicity has been implicated in a variety of conditions including epilepsy, stroke, ischemia, Huntington's disease, Parkinson's disease and Alzheimer's disease. Certain differentiated cells as made according to the methods described here may also be appropriate for treating dysmyelinating disorders, such as Pelizaeus-Merzbacher disease, multiple sclerosis, leukodystrophies, neuritis and neuropathies. Appropriate for these purposes are cell cultures enriched in oligodendrocytes or oligodendrocyte precursors to promote remyelination.

Hepatocytes and hepatocyte precursors prepared using our methods can be assessed in animal models for ability to repair liver damage. One such example is damage caused by intraperitoneal injection of D-galactosamine (Dabeva et al., Am. J. Pathol. 143:1606, 1993). Efficacy of treatment can be determined by immunohistochemical staining for liver cell markers, microscopic determination of whether canalicular structures form in growing tissue, and the ability of the treatment to restore synthesis of liver-specific proteins. Liver cells can be used in therapy by direct administration, or as part of a bioassist device that provides temporary liver function while the subject's liver tissue regenerates itself following fulminant hepatic failure.

The efficacy of cardiomyocytes prepared according to the methods described here can be assessed in animal models for cardiac cryoinjury, which causes 55% of the left ventricular wall tissue to become scar tissue without treatment (Li et al., Ann. Thorac. Surg. 62:654, 1996; Sakai et al., Ann. Thorac. Surg. 8:2074, 1999, Sakai et al., J. Thorac. Cardiovasc. Surg. 118:715, 1999). Successful treatment will reduce the area of the scar, limit scar expansion, and improve heart function as determined by systolic, diastolic, and developed pressure. Cardiac injury can also be modeled using an embolization coil in the distal portion of the left anterior descending artery (Watanabe et al., Cell Transplant. 7:239, 1998), and efficacy of treatment can be evaluated by histology and cardiac function. Cardiomyocyte preparations can be used in therapy to regenerate cardiac muscle and treat insufficient cardiac function (U.S. Pat. No. 5,919,449 and WO 99/03973).

Cancer

Progenitor cell lines and differentiated cells made by the methods and compositions described here may be used for the treatment of cancer.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia.

More particular examples of such cancers include squamous cell cancer, small-cell lung cancer, non-small cell lung cancer, gastric cancer, pancreatic cancer, glial cell tumors such as glioblastoma and neurofibromatosis, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma and various types of head and neck cancer. Further examples are solid tumor cancer including colon cancer, breast cancer, lung cancer and prostate cancer, hematopoietic malignancies including leukemias and lymphomas, Hodgkin's disease, aplastic anemia, skin cancer and familiar adenomatous polyposis. Further examples include brain neoplasms, colorectal neoplasms, breast neoplasms, cervix neoplasms, eye neoplasms, liver neoplasms, lung neoplasms, pancreatic neoplasms, ovarian neoplasms, prostatic neoplasms, skin neoplasms, testicular neoplasms, neoplasms, bone neoplasms, trophoblastic neoplasms, fallopian tube neoplasms, rectal neoplasms, colonic neoplasms, kidney neoplasms, stomach neoplasms, and parathyroid neoplasms. Breast cancer, prostate cancer, pancreatic cancer, colorectal cancer, lung cancer, malignant melanoma, leukaemia, lymphoma, ovarian cancer, cervical cancer and biliary tract carcinoma are also included.

In preferred embodiments, the progenitor cell lines and differentiated cells made according to the methods and compositions described here are used to treat T cell lymphoma, melanoma or lung cancer.

The progenitor cell lines and differentiated cells made according to the methods and compositions described here may also be used in combination with anticancer agents such as endostatin and angiostatin or cytotoxic agents or chemotherapeutic agent. For example, drugs such as such as adriamycin, daunomycin, cis-platinum, etoposide, taxol, taxotere and alkaloids, such as vincristine, and antimetabolites such as methotrexate. The term "cytotoxic agent" as used herein refers to a substance that inhibits or prevents the function of cells and/or causes destruction of cells. The term is intended to include radioactive isotopes (e.g. I, Y, Pr), chemotherapeutic agents, and toxins such as enzymatically active toxins of bacterial, fungal, plant or animal origin, or fragments thereof.

Also, the term includes oncogene product/tyrosine kinase inhibitors, such as the bicyclic ansamycins disclosed in WO 94/22867; 1,2-bis(arylamino) benzoic acid derivatives disclosed in EP 600832; 6,7-diamino-phthalazin-1-one derivatives disclosed in EP 600831; 4,5-bis(arylamino)-phthalimide derivatives as disclosed in EP 516598; or peptides which inhibit binding of a tyrosine kinase to a SH2-containing substrate protein (see WO 94/07913, for example). A "chemotherapeutic agent" is a chemical compound useful in the treatment of cancer. Examples of chemotherapeutic agents include Adriamycin, Doxorubicin, 5-Fluorouracil (5 FU), Cytosine arabinoside (Ara-C), Cyclophosphamide, Thiotepa, Busulfan, Cytoxin, Taxol, Methotrexate, Cisplatin, Melphalan, Vinblastine, Bleomycin, Etoposide, Ifosfamide, Mitomycin C, Mitoxantrone, Vincristine, VP-16, Vinorelbine, Carboplatin, Teniposide, Daunomycin, Carminomycin, Aminopterin, Dactinomycin, Mitomycins, Nicotinamide, Esperamicins (see U.S. Pat. No. 4,675,187), Melphalan and other related nitrogen mustards, and endocrine therapies (such as diethylstilbestrol (DES), Tamoxifen, LHRH antagonizing drugs, progestins, anti-progestins etc).

Stem Cells

As used in this document, the term "stem cell" refers to a cell that on division faces two developmental options: the daughter cells can be identical to the original cell (self-renewal) or they may be the progenitors of more specialised cell types (differentiation). The stem cell is therefore capable of adopting one or other pathway (a further pathway exists in which one of each cell type can be formed). Stem cells are therefore cells which are not terminally differentiated and are able to produce cells of other types.

Stem cells as referred to in this document may include totipotent stem cells, pluripotent stem cells, and multipotent stem cells.

Totipotent Stem Cells

The term "totipotent" cell refers to a cell which has the potential to become any cell type in the adult body, or any cell of the extraembryonic membranes (e.g., placenta). Thus, the only totipotent cells are the fertilized egg and the first 4 or so cells produced by its cleavage.

Pluripotent Stem Cells

"Pluripotent stem cells" are true stem cells, with the potential to make any differentiated cell in the body. However, they cannot contribute to making the extraembryonic membranes which are derived from the trophoblast. Several types of pluripotent stem cells have been found.

Embryonic Stem Cells

Embryonic Stem (ES) cells may be isolated from the inner cell mass (ICM) of the blastocyst, which is the stage of embryonic development when implantation occurs.

Embryonic Germ Cells

Embryonic Germ (EG) cells may be isolated from the precursor to the gonads in aborted fetuses.

Embryonic Carcinoma Cells

Embryonic Carcinoma (EC) cells may be isolated from teratocarcinomas, a tumor that occasionally occurs in a gonad of a fetus. Unlike the first two, they are usually aneuploid. All three of these types of pluripotent stem cells can only be isolated from embryonic or fetal tissue and can be grown in culture. Methods are known in the art which prevent these pluripotent cells from differentiating.

Adult Stem Cells

Adult stem cells comprise a wide variety of types including neuronal, skin and the blood forming stem cells which are the active component in bone marrow transplantation. These latter stem cell types are also the principal feature of umbilical cord-derived stem cells. Adult stem cells can mature both in the laboratory and in the body into functional, more specialised cell types although the exact number of cell types is limited by the type of stem cell chosen.

Multipotent Stem Cells

Multipotent stem cells are true stem cells but can only differentiate into a limited number of types. For example, the bone marrow contains multipotent stem cells that give rise to all the cells of the blood but not to other types of cells. Multipotent stem cells are found in adult animals. It is thought that every organ in the body (brain, liver) contains them where they can replace dead or damaged cells.

Methods of characterising stem cells are known in the art, and include the use of standard assay methods such as clonal assay, flow cytometry, long-term culture and molecular biological techniques e.g. PCR, RT-PCR and Southern blotting.

In addition to morphological differences, human and murine pluripotent stem cells differ in their expression of a number of cell surface antigens (stem cell markers). Antibodies for the identification of stem cell markers including the Stage-Specific Embryonic Antigens 1 and 4 (SSEA-1 and SSEA-4) and Tumor Rejection Antigen 1-60 and 1-81 (TRA-1-60, TRA-1-81) may be obtained commercially, for example from Chemicon International, Inc (Temecula, Calif., USA). The immunological detection of these antigens using monoclonal antibodies has been widely used to characterize pluripotent stem cells (Shamblott M. J. et, al. (1998) PNAS 95: 13726-13731; Schuldiner M. et. al. (2000). PNAS 97: 11307-11312; Thomson J. A. et. al. (1998). Science 282: 1145-1147; Reubinoff B. E. et. al. (2000). Nature Biotechnology 18: 399-404; Henderson J. K. et. al. (2002). Stem Cells 20: 329-337; Pera M, et. al. (2000). J. Cell Science 113: 5-10).

Sources of Stem Cells

Stem cells of various types, which may include the following non-limiting examples, may be used in the methods and compositions described here for producing progenitor cells, progenitor cell lines and differentiated cells.

U.S. Pat. No. 5,851,832 reports multipotent neural stem cells obtained from brain tissue. U.S. Pat. No. 5,766,948 reports producing neuroblasts from newborn cerebral hemispheres. U.S. Pat. Nos. 5,654,183 and 5,849,553 report the use of mammalian neural crest stem cells. U.S. Pat. No. 6,040,180 reports in vitro generation of differentiated neurons from cultures of mammalian multipotential CNS stem cells. WO 98/50526 and WO 99/01159 report generation and isolation of neuroepithelial stem cells, oligodendrocyte-astrocyte precursors, and lineage-restricted neuronal precursors. U.S. Pat. No. 5,968,829 reports neural stem cells obtained from embryonic forebrain and cultured with a medium comprising glucose, transferrin, insulin, selenium, progesterone, and several other growth factors.

Primary liver cell cultures can be obtained from human biopsy or surgically excised tissue by perfusion with an appropriate combination of collagenase and hyaluronidase. Alternatively, EP 0 953 633 A1 reports isolating liver cells by preparing minced human liver tissue, resuspending concentrated tissue cells in a growth medium and expanding the cells in culture. The growth medium comprises glucose, insulin, transferrin, $T_3$, FCS, and various tissue extracts that allow the hepatocytes to grow without malignant transformation. The cells in the liver are thought to contain specialized cells including liver parenchymal cells, Kupffer cells, sinusoidal endothelium, and bile duct epithelium, and also precursor cells (referred to as "hepatoblasts" or "oval cells") that have the capacity to differentiate into both mature hepatocytes or biliary epithelial cells (L. E. Rogler, Am. J. Pathol. 150:591, 1997; M. Alison, Current Opin. Cell Biol. 10:710, 1998; Lazaro et al., Cancer Res. 58:514, 1998).

U.S. Pat. No. 5,192,553 reports methods for isolating human neonatal or fetal hematopoietic stem or progenitor cells. U.S. Pat. No. 5,716,827 reports human hematopoietic cells that are Thy-1 positive progenitors, and appropriate growth media to regenerate them in vitro. U.S. Pat. No. 5,635, 387 reports a method and device for culturing human hematopoietic cells and their precursors. U.S. Pat. No. 6,015,554 describes a method of reconstituting human lymphoid and dendritic cells.

U.S. Pat. No. 5,486,359 reports homogeneous populations of human mesenchymal stem cells that can differentiate into cells of more than one connective tissue type, such as bone, cartilage, tendon, ligament, and dermis. They are obtained from bone marrow or periosteum. Also reported are culture conditions used to expand mesenchymal stem cells. WO 99/01145 reports human mesenchymal stem cells isolated from peripheral blood of individuals treated with growth factors such as G-CSF or GM-CSF. WO 00/53795 reports adipose-derived stem cells and lattices, substantially free of adipocytes and red cells. These cells reportedly can be expanded and cultured to produce hormones and conditioned culture media.

Stem cells of any vertebrate species can be used. Included are stem cells from humans; as well as non-human primates, domestic animals, livestock, and other non-human mammals.

Amongst the stem cells suitable for use in this invention are primate pluripotent stem (pPS) cells derived from tissue formed after gestation, such as a blastocyst, or fetal or embryonic tissue taken any time during gestation. Non-limiting examples are primary cultures or established lines of embryonic stem cells.

Media and Feeder Cells

Media for isolating and propagating pPS cells can have any of several different formulas, as long as the cells obtained have the desired characteristics, and can be propagated further. Suitable sources are as follows: Dulbecco's modified Eagles medium (DMEM), Gibco #11965-092; Knockout Dulbecco's modified Eagles medium (KO DMEM), Gibco #10829-018; 200 mM L-glutamine, Gibco #15039-027; non-essential amino acid solution, Gibco 11140-050; beta-mercaptoethanol, Sigma #M7522; human recombinant basic fibroblast growth factor (bFGF), Gibco #13256-029. Exemplary serum-containing embryonic stem (ES) medium is made with 80% DMEM (typically KO DMEM), 20% defined fetal bovine serum (PBS) not heat inactivated, 0.1 mM non-essential amino acids, 1 mM L-glutamine, and 0.1 mM beta-mercaptoethanol. The medium is filtered and stored at 4 degrees C. for no longer than 2 weeks, Serum-free embryonic stem (ES) medium is made with 80% KO DMEM, 20% serum replacement, 0.1 mM non-essential amino acids, 1 mM L-glutamine, and 0.1 mM beta-mercaptoethanol. An effective serum replacement is Gibco #10828-028. The medium is filtered and stored at 4 degrees C. for no longer than 2 weeks. Just before use, human bFGF is added to a final concentration of 4 ng/mL (Bodnar et al., Geron Corp, International Patent Publication WO 99/20741).

Feeder cells (where used) are propagated in mEF medium, containing 90% DMEM (Gibco #11965-092), 10% FBS (Hyclone #30071-03), and 2 mM glutamine. mEFs are propagated in T150 flasks (Corning #430825), splitting the cells 1:2 every other day with trypsin, keeping the cells subconfluent. To prepare the feeder cell layer, cells are irradiated at a dose to inhibit proliferation but permit synthesis of important factors that support human embryonic stem cells (.about.4000 rads gamma irradiation). Six-well culture plates (such as Falcon #304) are coated by incubation at 37 degrees C. with 1 mL 0.5% gelatin per well overnight, and plated with 375,000 irradiated mEFs per well. Feeder cell layers are typically used 5 h to 4 days after plating. The medium is replaced with fresh human embryonic stem (hES) medium just before seeding pPS cells.

Conditions for culturing other stem cells are known, and can be optimized appropriately according to the cell type. Media and culture techniques for particular cell types referred to in the previous section are provided in the references cited.

Embryonic Stem Cells

Embryonic stem cells can be isolated from blastocysts of members of the primate species (Thomson et al., Proc. Natl. Acad. Sci. USA 92:7844, 1995). Human embryonic stem (hES) cells can be prepared from human blastocyst cells using the techniques described by Thomson et al. (U.S. Pat. No. 5,843,780; Science 282:1145, 1998; Curr. Top. Dev. Biol. 38:133 f1, 1998) and Reubinoff et al, Nature Biotech. 18:399, 2000.

Briefly, human blastocysts are obtained from human in vivo preimplantation embryos. Alternatively, in vitro fertilized (IVF) embryos can be used, or one cell human embryos can be expanded to the blastocyst stage (Bongso et al., Hum Reprod 4: 706, 1989). Human embryos are cultured to the blastocyst stage in G1.2 and G2.2 medium (Gardner et al., Perth. Steril. 69:84, 1998). Blastocysts that develop are selected for embryonic stem cell isolation. The zona pellucida is removed from blastocysts by brief exposure to pronase (Sigma). The inner cell masses are isolated by immunosurgery, in which blastocysts are exposed to a 1:50 dilution of rabbit anti-human spleen cell antiserum for 30 minutes, then washed for 5 minutes three times in DMEM, and exposed to a 1:5 dilution of Guinea pig complement (Gibco) for 3 minutes (see Solter et al., Proc. Natl. Mad. Sci. USA 72:5099, 1975). After two further washes in DMEM, lysed trophectoderm cells are removed from the intact inner cell mass (ICM) by gentle pipetting, and the ICM plated on mRF feeder layers.

After 9 to 15 days, inner cell mass-derived outgrowths are dissociated into clumps either by exposure to calcium and magnesium-free phosphate-buffered saline (PBS) with 1 mM EDTA, by exposure to dispase or trypsin, or by mechanical dissociation with a micropipette; and then replated on mEF in fresh medium. Dissociated cells are replated on mEF feeder layers in fresh embryonic stem (ES) medium, and observed for colony formation. Colonies demonstrating undifferentiated morphology are individually selected by micropipette, mechanically dissociated into clumps, and replated, embryonic stem cell-like morphology is characterized as compact colonies with apparently high nucleus to cytoplasm ratio and prominent nucleoli. Resulting embryonic stem cells are then routinely split every 1-2 weeks by brief trypsinization, exposure to Dulbecco's PBS (without calcium or magnesium and with 2 mM EDTA), exposure to type IV collagenase (.about.200 U/mL; Gibco) or by selection of individual colonies by micropipette. Clump sizes of about 50 to 100 cells are optimal.

Embryonic Germ Cells

Human Embryonic Germ (hEG) cells can be prepared from primordial germ cells present in human fetal material taken about 8-11 weeks after the last menstrual period. Suitable preparation methods are described in Shamblott et al., Proc. Natl. Acad. Sci. USA 95:13726, 1998 and U.S. Pat. No. 6,090,622.

Briefly, genital ridges are rinsed with isotonic buffer, then placed into 0.1 mL 0.05% trypsin/0.53 mM sodium EDTA solution (BRL) and cut into <1 mm$^3$ chunks. The tissue is then pipetted through a 100/µL tip to further disaggregate the cells. It is incubated at 37 degrees C. for about 5 min, then about 3.5 mL EG growth medium is added. EG growth medium is DMEM, 4500 mg/L D-glucose, 2200 mg/L mM sodium bicarbonate; 15% embryonic stem (ES) qualified fetal calf serum (BRL); 2 mM glutamine (BRL); 1 mM sodium pyruvate (BRL); 1000-2000 U/mL human recombinant leukemia inhibitory factor (LIF, Genzyme); 1-2 ng/ml human recombinant basic fibroblast growth factor (bFGF, Genzyme); and 10 µM forskolin (in 10% DMSO). In an alternative approach, EG cells are isolated using hyaluronidase/collagenase/DNAse. Gonadal anlagen or genital ridges with mesenteries are dissected from fetal material, the genital ridges are rinsed in PBS, then placed in 0.1 ml HCD digestion solution (0.01% hyaluronidase type V, 0.002% DNAse I, 0.1% collagenase type IV, all from Sigma prepared in EG growth medium), Tissue is minced and incubated 1 h or overnight at 37 degrees C., resuspended in 1-3 mL of EG growth medium, and plated onto a feeder layer.

Ninety-six well tissue culture plates are prepared with a sub-confluent layer of feeder cells cultured for 3 days in modified EG growth medium free of LIF, bFGF or forskolin, inactivated with 5000 rad y-irradiation. Suitable feeders are STO cells (ATCC Accession No. CRL 1503). 0.2 mL of primary germ cell (PGC) suspension is added to each of the wells. The first passage is conducted after 7-10 days in EG growth medium, transferring each well to one well of a 24-well culture dish previously prepared with irradiated STO mouse fibroblasts. The cells are cultured with daily replacement of medium until cell morphology consistent with EG cells are observed, typically after 7-30 days or 1-4 passages.

Self-Renewal and Differentiation

Self-Renewal

Stem cells which are self-renewing may be identified by various means known in the art, for example, morphology, immunohistochemistry, molecular biology, etc.

Such stem cells preferably display increased expression of Oct4 and/or SSEA-1. Preferably, expression of any one or more of Flk-1, Tie-2 and c-kit is decreased. Stem cells which are self-renewing preferably display a shortened cell cycle compared to stem cells which are not self-renewing.

For example, in the two dimensions of a standard microscopic image, human embryonic stem cells display high nuclear/cytoplasmic ratios in the plane of the image, prominent nucleoli, and compact colony formation with poorly discernable cell junctions. Cell lines can be karyotyped using a standard G-banding technique (available at many clinical diagnostics labs that provides routine karyotyping services, such as the Cytogenetics Lab at Oakland Calif.) and compared to published human karyotypes.

Human embryonic stem and human embryonic germ cells may also be characterized by expressed cell markers. In general, the tissue-specific markers discussed in this disclosure can be detected using a suitable immunological technique—such as flow cytometry for membrane-bound markers, immunohistochemistry for intracellular markers, and enzyme-linked immunoassay, for markers secreted into the medium. The expression of protein markers can also be detected at the mRNA level by reverse transcriptase-PCR using marker-specific primers. See U.S. Pat. No. 5,843,780 for further details.

Stage-specific embryonic antigens (SSEA) are characteristic of certain embryonic cell types. Antibodies for SSEA markers are available from the Developmental Studies Hybridoma Bank (Bethesda Md.). Other useful markers are detectable using antibodies designated Tra-1-60 and Tra-1-81 (Andrews et al., Cell Linesfrom Human Gem Cell Tumors, in E. L Robertson, 1987, supra). Human embryonic stem cells are typically SSEA-1 negative and SSEA-4 positive. hEG cells are typically SSEA-1 positive. Differentiation of pPS cells in vitro results in the loss of SSEA-4, Tra-1-60, and Tra-1-81 expression and increased expression of SSEA-1. pPS cells can also be characterized by the presence of alkaline phosphatase activity, which can be detected by fixing the cells with 4% paraformaldehyde, and then developing with Vector Red as a substrate, as described by the manufacturer (Vector Laboratories, Burlingame Calif.).

Embryonic stem cells are also typically telomerase positive and OCT-4 positive. Telomerase activity can be determined using TRAP activity assay (Kim et al., Science 266:2011, 1997), using a commercially available kit (TRAPeze® XK. Telomerase Detection Kit, Cat. s7707; Intergen Co., Purchase N.Y.; or TeloTAGGG™ Telomerase PCR ELISA plus, Cat 2,013,89; Roche Diagnostics, Indianapolis). hTERT expression can also be evaluated at the mRNA level by RT-PCR. The LightCycler TeloTAGGG™ hTERT quantification kit (Cat. 3,012,344; Roche Diagnostics) is available commercially for research purposes.

Differentiation

Differentiating cells, including progenitor cell lines and differentiated cells derived from these, preferably display enhanced dephosphorylation of 4E-BP1 and/or S6K1. They preferably display decreased expression of Oct4 and/or SSEA-1. Preferably, expression of any one or more of Flk-1, Tie-2 and c-kit is increased. Preferably, expression of any one or more of Brachyury, AFP, nestin and nurr1 expression increased. Stem cells which are self-renewing preferably display a lengthened cell cycle compared to stem cells which are not self-renewing.

Differentiating stem cells, i.e., cells which have started to, or are committed to a pathway of differentiation can be characterized according to a number of phenotypic criteria, including in particular transcript changes. The criteria include but are not limited to characterization of morphological features, detection or quantitation of expressed cell markers and enzymatic activity, gene expression and determination of the functional properties of the cells in vivo. In general, differentiating stem cells will have one or more features of the cell type which is the final product of the differentiation process, i.e., the differentiated cell. For example, if the target cell type is a muscle cell, a stem cell which is in the process of differentiating to such a cell will have for example a feature of myosin expression.

In many respects, therefore, the criteria will depend on the fate of the differentiating stem cell, and a general description of various cell types is provided below.

Markers of interest for differentiated or differentiating neural cells include beta-tubulin EIII or neurofilament, characteristic of neurons; glial fibrillary acidic protein (GFAP), present in astrocytes; galactocerebroside (GalC) or myelin basic protein (MBP); characteristic of oligodendrocytes; OCT-4, characteristic of undifferentiated human embryonic stem cells; nestin, characteristic of neural precursors and other cells. A2B5 and NCAM are characteristic of glial progenitors and neural progenitors, respectively. Cells can also be tested for secretion of characteristic biologically active substances. For example, GABA-secreting neurons can be identified by production of glutamic acid decarboxylase or GABA. Dopaminergic neurons can be identified by production of dopa decarboxylase, dopamine, or tyrosine hydroxylase.

Markers of interest for differentiated or differentiating liver cells include alpha-fetoprotein (liver progenitors); albumin, $\alpha_1$-antitrypsin, glucose-6-phosphatase, cytochrome p450 activity, transferrin, asialoglycoprotein receptor, and glycogen storage (hepatocytes); CK7, CK19, and gamma-glutamyl transferase (bile epithelium). It has been reported that hepatocyte differentiation requires the transcription factor BNF-4 alpha (Li et al., Genes Dev. 14:464, 2000). Markers independent of HNF-4 alpha expression include alpha$_1$-antitrypsin, alpha-fetoprotein, apoE, glucokinase, insulin growth factors 1 and 2, IGF-1 receptor, insulin receptor, and leptin. Markers dependent on HNF-4 alpha expression include albumin, apoAI, apoAII, apoB, apoCIII, apoCII, aldolase B, phenylalanine hydroxylase, L-type fatty acid binding protein, transferrin, retinol binding protein, and erythropoietin (EPO).

Cell types in mixed cell populations derived from pPS cells can be recognized by characteristic morphology and the markers they express. For skeletal muscle: myoD, myogenin, and myf-5. For endothelial cells: PECAM (platelet endothelial cell adhesion molecule), Flk-1, tie-i, tie-2, vascular endothelial (VE) cadherin, MECA-32, and MEC-14.7. For smooth muscle cells: specific myosin heavy chain. For cardiomyocytes: GATA-4, Nkx2.5, cardiac troponin I, alpha-myosin heavy chain, and ANF. For pancreatic cells, pdx and insulin secretion. For hematopoietic cells and their progenitors: GATA-1, CD34, AC133, β-major globulin, and β-major globulin like gene PH1.

Certain tissue-specific markers listed in this disclosure or known in the art can be detected by immunological techniques—such as flow immunocytochemistry for cell-surface markers, immunohistochemistry (for example, of fixed cells or tissue sections) for intracellular or cell-surface markers, Western blot analysis of cellular extracts, and enzyme-linked immunoassay, for cellular extracts or products secreted into the medium. The expression of tissue-specific gene products can also be detected at the mRNA level by Northern blot analysis, dot-blot hybridization analysis, or by reverse transcriptase initiated polymerase chain reaction (RT-PCR) using sequence-specific primers in standard amplification methods. Sequence data for the particular markers listed in this disclosure can be obtained from public databases such as GenBank (URL www.ncbi.nlm.nih.gov:80/entrez).

EXAMPLES

Example 1

Methods: Derivation of E-RoSH Cell Lines

Embryonic stem cells (ESCs) are induced to differentiate to form embryoid bodies (Ebs) using the methylcellulose-based approach described in Lim et al, Blood. 1997; 90:1291-1299)

Day 3 to day 6 embryoid bodies are harvested, dissociated into single cell suspensions by collagenase digestion (Robertson E J. Embryo-derived stem cell lines. In: Robertson E J, ed. Teratocarcinomas and embryonic stem cells: a practical approach. Oxford: IRL Press Limited; 1987:71-112) and plated on at a density of $1-5 \times 10^5$ cells per 10 cm feeder plate. After about a week, the cells proliferated and differentiated into a complex mixture of cell types.

Colonies of rapidly dividing cells resembling embryo-derived RoSH cells are picked and expanded sequentially to a 48-well plate, 24-well plate, 6-well plate and then a 10 cm plate. The culture from each colony is named E-RoSH1, 2, 3 . . . in the sequence in which each culture is established.

Each of these cell cultures are then replated at 10-100 cells per 10 cm plate. Colonies are then selected and expanded to establish sublines that are named based on their parental lines e.g. E-RoSH1.1, 1.2, 1.3, etc. For suspension cultures, $1 \times 10^6$ cells are plated on 10 cm bacterial Petri dishes that are placed on an orbital shaker.

Alkaline phosphatase assay, and MITT assays are performed using assay kits from Chemicon (Temecula, Calif.) and Bioassay Systems (Hayward, Calif.). Chromosomes counting is performed as previously described (Robertson, supra).

Example 2

Methods: Derivation of HuES9.E Mesenchymal Stem Cell (MSC)-Like Cell Lines

HuES9 cells are cultured as previously described in Cowan et al, N Engl J Med. 2004; 350:1353-1356.

To derive HuES9.E MSC-like cells, HuES9 cells are split 1:4 onto gelatinized feeder-free plates in using HuES9 culture media. Confluent cultures are trypsinized and split 1:4. Differentiation into adipocytes, and osteocytes is performed as previously described (Barberi et al, PLoS Med. 2005; 2:e161).

BM MSCs are prepared as previously described in Pittenger et al, Science. 1999; 284:143-147.

Genomic PCR for mouse- and human-specific repeat sequences are performed as previously described in Que et al, in Vitro Cell Dev Biol Anim. 2004; 40:143-149.

Example 3

Methods: RT-PCR Analysis

Total RNA is prepared using standard protocols and are quantified using, respectively, the RiboGreen RNA Quantification kit and the PicoGreen dsDNA Quantification kit (Molecular Probes, Eugene, Oreg.).

Quantitative RT-PCR is performed using TaqMan® primers (Applied Biosystems, Foster City, Calif.).

Example 4

Methods: In Vitro Endothelial Differentiation

Endothelial differentiation of E-RoSH cells and acetylated LDL uptake by differentiated E-RoSH cells are performed as previously described (Yin et al, Arterioscler Thromb Vase Biol. 2004; 24:691-696)

In vitro differentiated E-RoSH vascular structures are fixed in formalin, embedded in paraffin, sectioned at 4 μm and stained for vWF using polyclonal, rabbit-generated antibody and Envision+ System-peroxidase (DakoCytomation, Gostrup, Denmark). The sections are counterstained with Mayer's hematoxylin.

Example 5

Methods: In Vivo Endothelial Differentiation $1 \times 10^6$ embryonic stem cells are transplanted subcutaneously into SCID mice. At three weeks when embryonic stem cell-derived tumors are about 1 cm in diameter, $1 \times 10^5$ E-RoSH cells labeled with Qdot® nanocrystals (655 nm emission) using a Qtracker® Cell Labeling Kit (Quantum Dot Corp, Hayward, Calif.) are injected into the embryonic stem cell-derived teratoma.

Three days later, the mice are euthanized with an overdose of anesthesia and the tumors are removed. The tumors are fixed in 4% paraformaldehyde and cryosectioned at 20 μm thickness. The sections are assayed for pecam-1 immunoreactivity using rat anti-pecam1 (Pharmingen, San Diego, Calif.) followed by FITC-conjugated rabbit anti-rat antibody (Chemicon, Temecula, Calif.), and counterstained with DAPI. The sections are analyzed by confocal microscopy.

Example 6

Derivation of Lineage-Restricted Endothelial Progenitor Cell Lines from Mouse Embryonic Stem Cells (mESCs)

To derive endothelial progenitor cell lines from mouse embryonic stem cells (mESCs), we relied on our previous experience of deriving RoSH endothelial progenitor cell lines from 5.5 dpc delayed blastocysts and early post-implantation mouse embryos (Yin et al, Arterioscler Thromb Vase Biol. 2004; 24:691-696).

We rationalized that since differentiation of embryonic stem cells (ESCs) into embryoid bodies (EBs) recapitulates some of early events in mammalian development, 3 to 6 days old embryoid bodies that are developmentally analogous to 5.5 dpc delayed blastocysts and early post-implantation embryos, will be enriched for cells that gave rise to RoSH progenitor cells. Therefore, 3 to 6 day old embryoid bodies are generated using a semi-solid, methylcellulose-based media (Lim et al, Blood. 1997; 90:1291-1299), dissociated into cell suspensions by collagenase digestion to disrupt the differentiating microenvironment of the embryoid bodies, and plated on gelatinized tissue culture plate at a density of $1-5 \times 10^5$ cells per 10 cm plate in embryonic stem (ES) media without LIF supplementation to discourage propagation of mouse embryonic stem cells (FIG. 1A).

Propagation of dissociated cells is enhanced if they are plated on embryonic fibroblast feeder as previously noted for the derivation of RoSH progenitor cells (Yin et al, Arterioscler Thromb Vase Biol. 2004; 24:691-696) but this tended to encourage growth of embryonic stem cells. After about a week, most of the cells differentiated into a heterogenous cell culture.

Figure 1B:
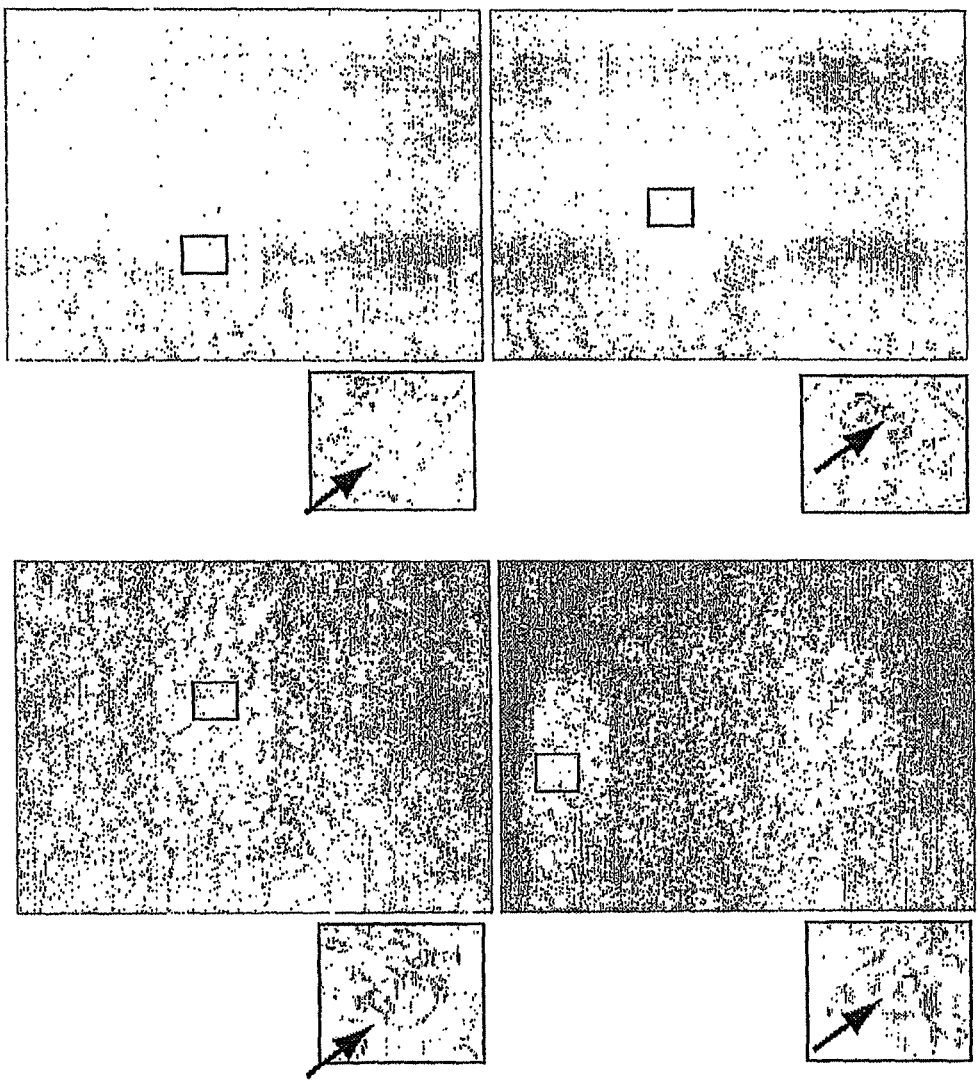
FIG. 1B. A putative RoSH-like colony consisting of adherent short fibroblast-like cells with characteristic ring-like cells (inset) expanding over time.

The cultures are then screened for RoSH-like colonies of rapidly dividing cells with large nucleus to cytoplasm ratio and ring-like cells that are immunoreactive for von Willebrand Factor (or vWF) (Yin et al, Arterioscler Thromb Vase Biol. 2004; 24:691-696) (FIG. 1B).

Only colonies that maintained a steady rate of proliferation and a stable morphology are selected when they reached a size of 2-300 cells, and expanded on either embryonic fibroblast feeder or gelatin-coated plates to generate lines, E-RoSH 1, 2, . . . etc.

Each of these lines is then subcloned by plating the cells at a low density of 10-100 cells per 10 cm plate, and colonies are then picked to derive sublines E-RoSH11.1, 1.2 etc. Alternatively, it is possible to enrich for self-renewing RoSH-like cells by passaging at 1:4 about two or three times before cloning by plating at low density. The most efficient yield of about one RoSH-like colony per $1-5 \times 10^5$ embryoid body cells is dependant on the age of embryoid bodies and the parental embryonic stem lines. For example, D3 to D5 embryoid bodies derived from the E14 embryonic stem cell line and D6 embryoid bodies derived from the CSL3 embryonic stem cell line (Bourc'his et al, Science. 2001; 294:2536-2539) are most efficient for derivation of RoSH-like lines.

On the other hand, derivation of RoSH-like lines from differentiating embryonic stem cells grown in the absence of LIF or other developmental stages of embryoid bodies is possible but much less efficient. We have established nine independently derived lines, five from CSL3 embryonic stem cell line and four from E14 embryonic stem cell line.

Example 7

Characterisation of E-RoSH Endothelial Progenitor Cells

Figure 1C:
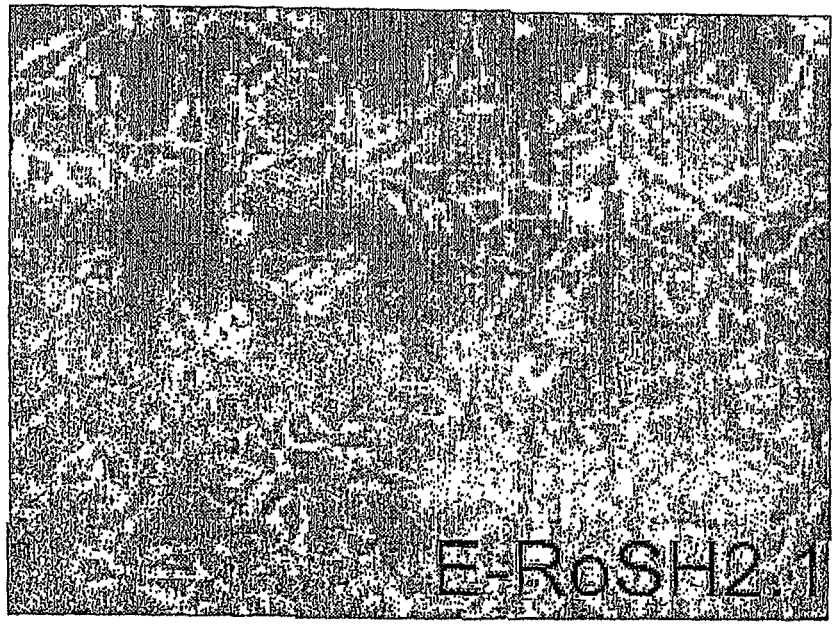
FIG. 1C. Morphological similarity between E-RoSH2.1 and RoSH2 cells in sub-confluent cultures.
Figure 1C:
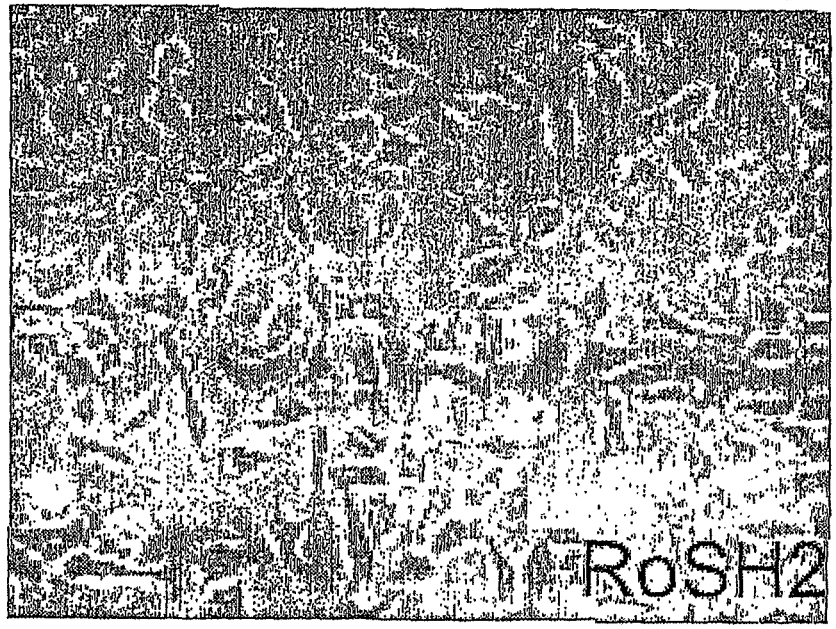
Figure 1D:
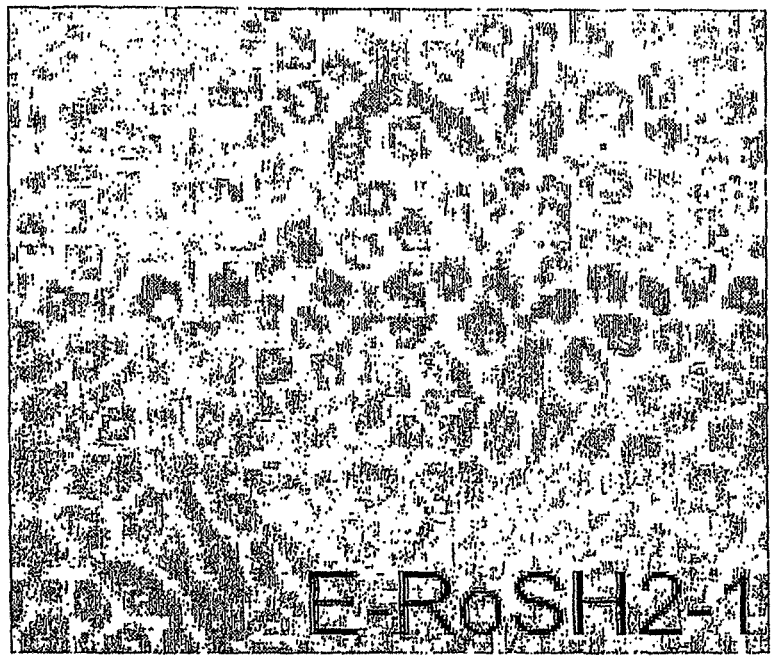
FIG. 1D. Alkaline phosphatase staining of E-RoSH2.1 and its parental E14 embryonic stem cells.
Figure 1D:
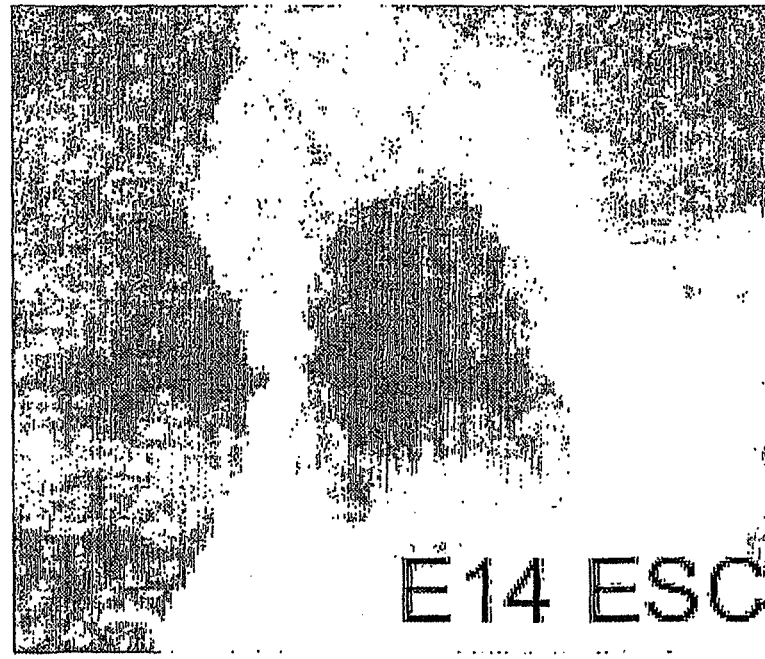

E-RoSH cells, as typified by E-RoSH2.1, are morphologically similar to embryo-derived RoSH cell lines (FIG. 1C), and unlike their parental embryonic stem cell lines, do not have detectable alkaline phosphatase activity (FIG. 1D).

Population doubling time is estimated be ~15 hours by MTT assay (data not shown). E-RoSH cells have been maintained in continuous culture for >40 generations by passaging every two days at 1:4 to 1:5 split (data not shown).

The karyotype of E-RoSH 2.1 and 3.2 as monitored by chromosome number, is stable for at least 10 passages with a normal mean chromosome number of 40 (FIG. 1E).

Figure 2A:
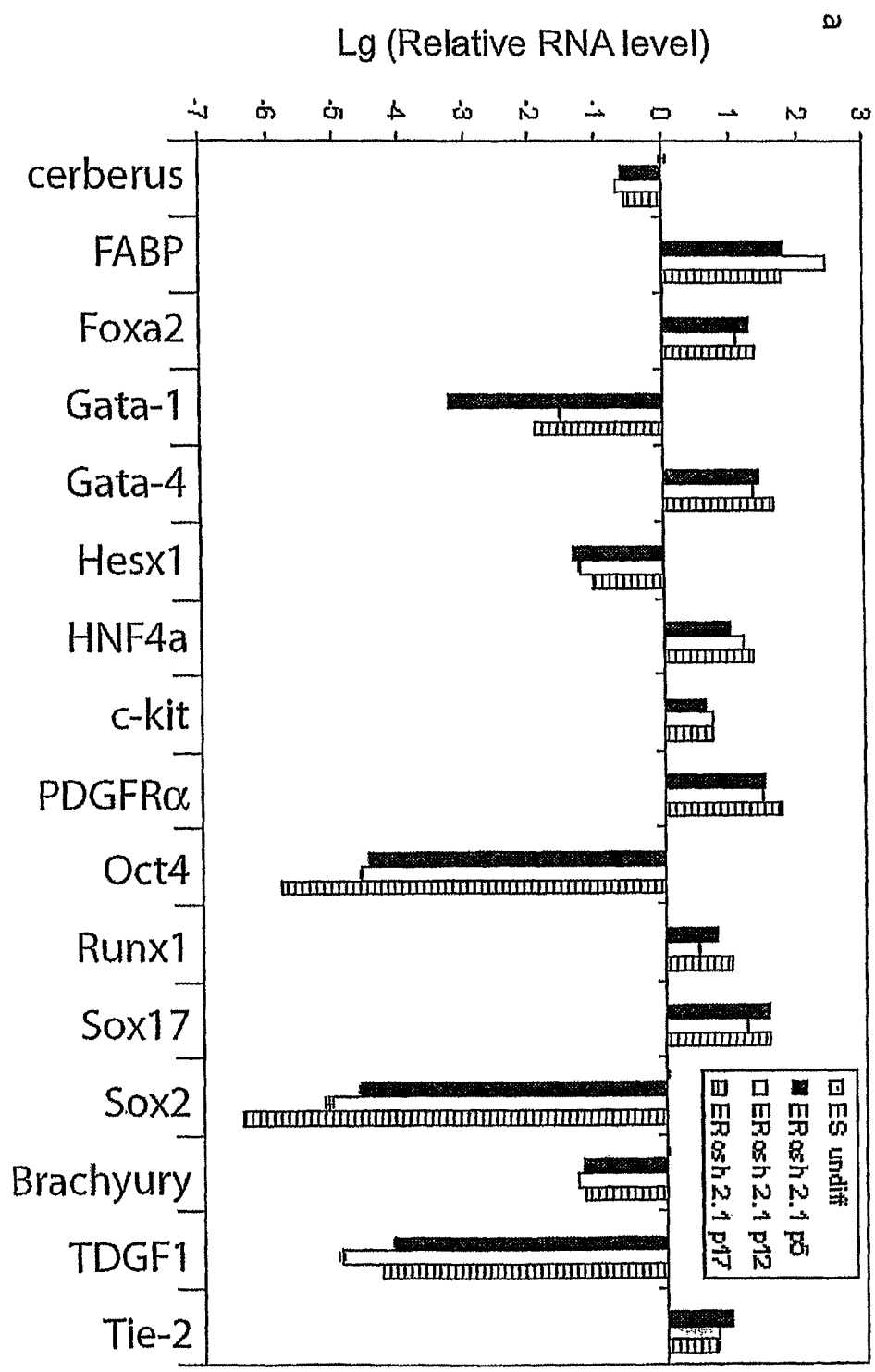
FIG. 2A. Gene expression profile of E-RoSH2.1 cells at three different passages.
Figure 2B:
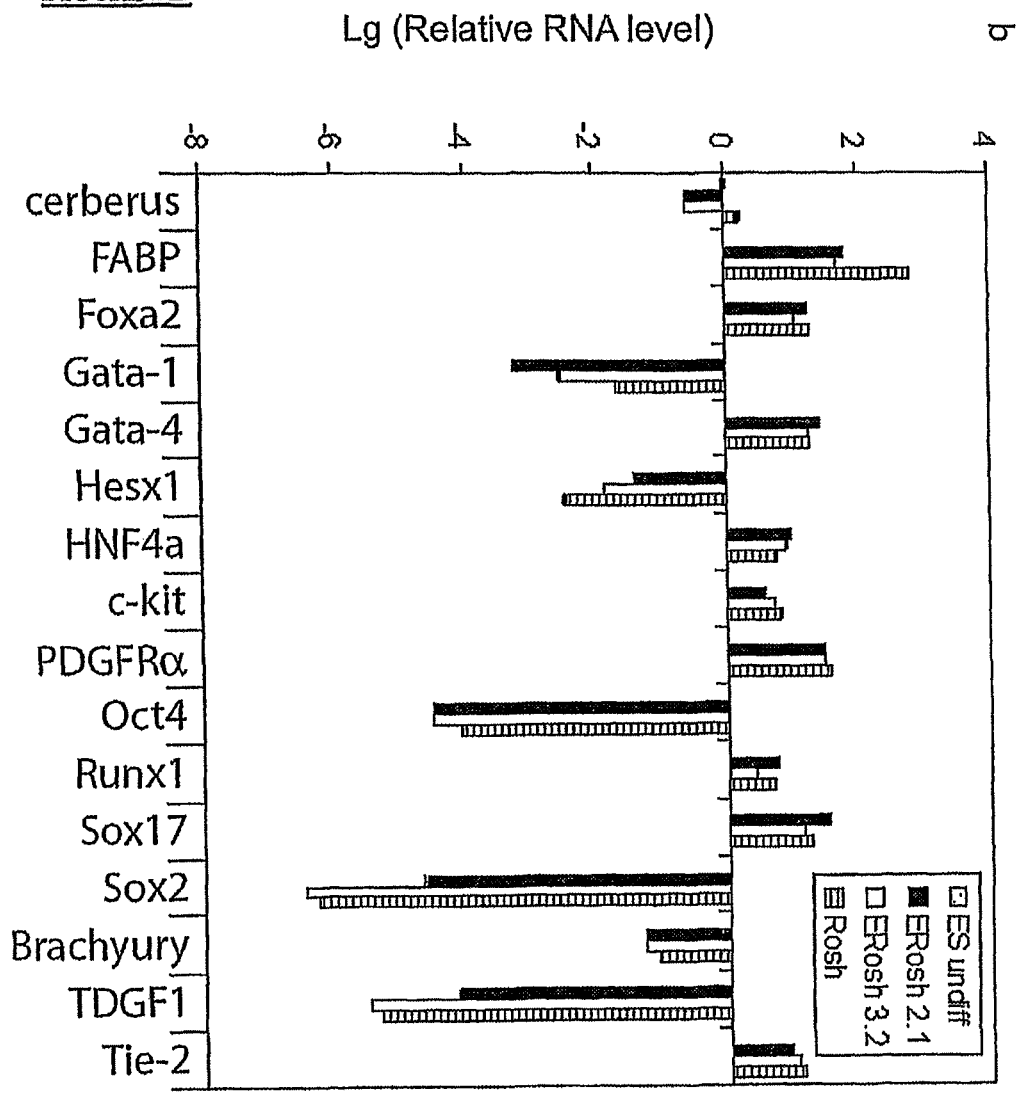
FIG. 2B. Comparative gene expression profiles in E-RoSH2.1, E-RoSH3.2 and RoSH2 cells.

Gene expression in E-RoSH2.1 is monitored by quantitative RT-PCR analysis of 15 genes and shown to be stable at different passages (FIG. 2A). In addition, this gene expression profile is similar to that in other independently derived E-RoSH lines as well as the mouse embryo-derived RoSH lines (FIG. 2B).

Subcutaneous transplantation of E-RoSH cells into SCID or Rag1−/− immunodeficient mice did not induce teratoma formation during a two to nine-months' observation period while similar transplantation of the parental embryonic stem cells will invariably generate a 2 cm teratoma within three weeks, suggesting a loss of pluripotency in E-RoSH cells (data not shown).

Figure 2C:
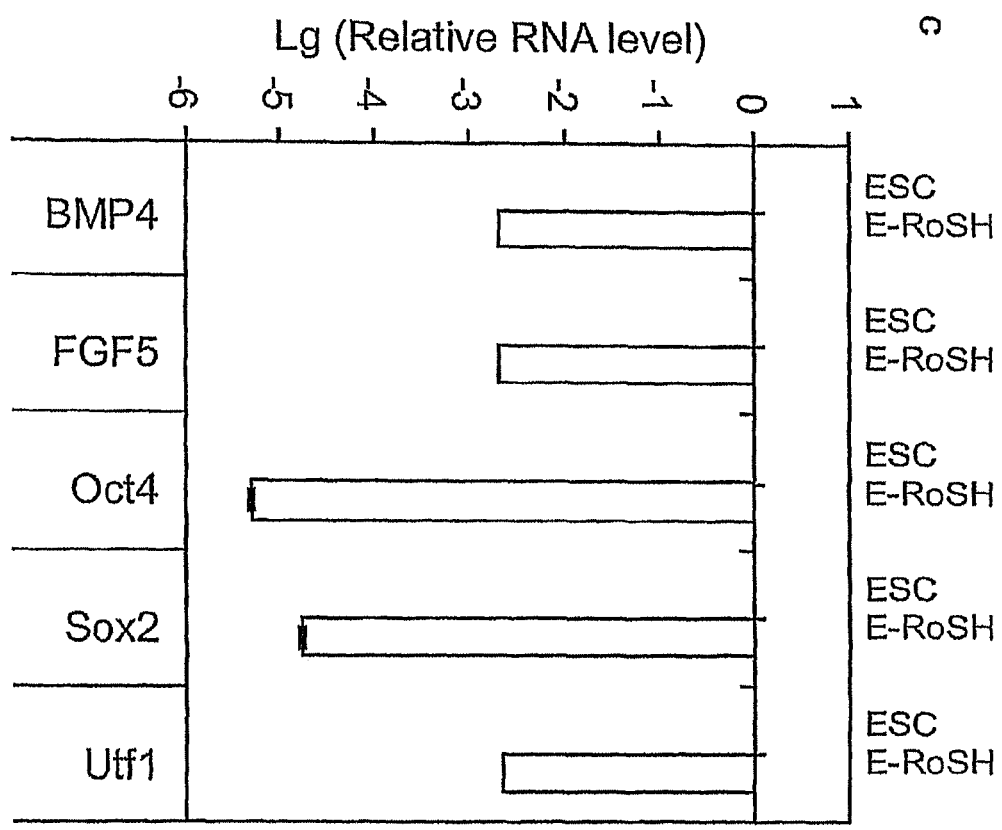
FIG. 2C and FIG. 2D Relative expression of genes associated with pluripotency and endothelial potential in the parental E14 embryonic stem cells and E-RoSH2.1 cells as measured by quantitative RT-PCR analysis.

This loss of pluripotency is further evidenced by reduced expression of several genes associated with pluripotent cells such as BMP4, FGF5, Oct4, Sox-2 and Utf1 (FIG. 2C) (Wei D, Xu G L, Lin C S, Bollman B, Bestor T H. Dnmt3L and the establishment of maternal genomic imprints. Stem Cells. 2005; 23:166-185; Rao M. Dev Biol. 2004; 275:269-286).

Figure 2D:
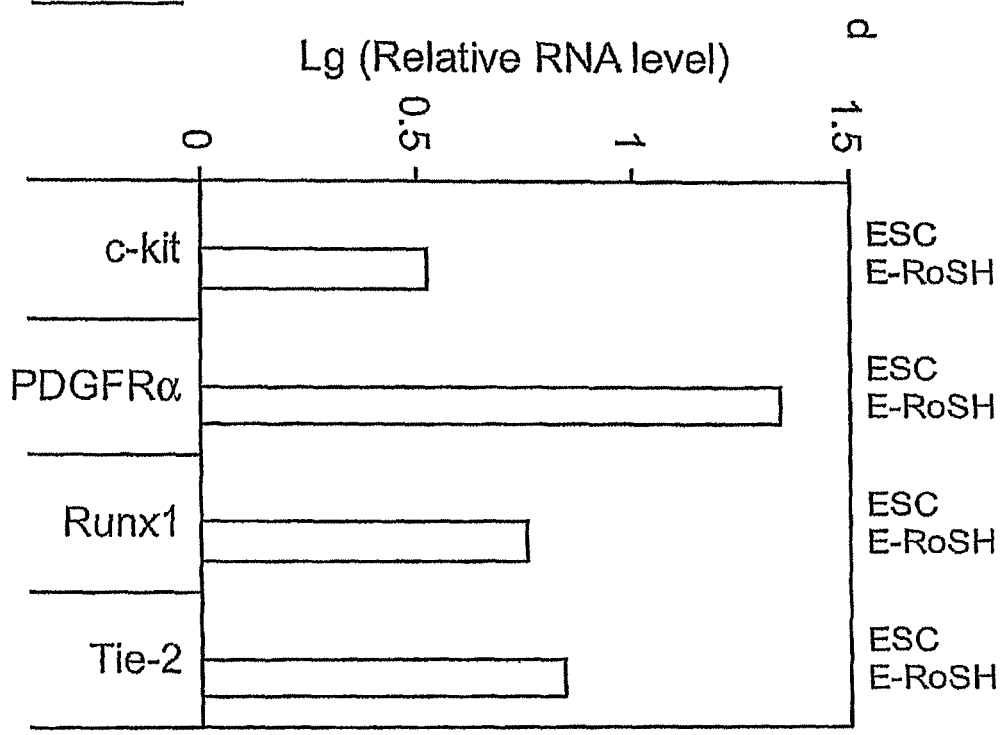

In contrast, a set of genes consisting of runx-1, flk-1, PDGFRα, Tie-2, and c-kit whose expression is commonly associated with endothelial progenitor cells (Jaffredo et al, Int J Dev Biol. 2005; 49:269-277), is highly expressed (FIG. 2D).

Together these observations demonstrate that E-RoSH cells are embryonic stem cell-derivatives that are no longer pluripotent and have a restricted differentiation potential that is likely to include endothelial potential.

Example 8

Differentiation of E-RoSH Cells into Endothelial Cells In Vitro and In Vivo

To confirm their endothelial potential, E-RoSH cells are plated on matrigel.

Figure 3A:
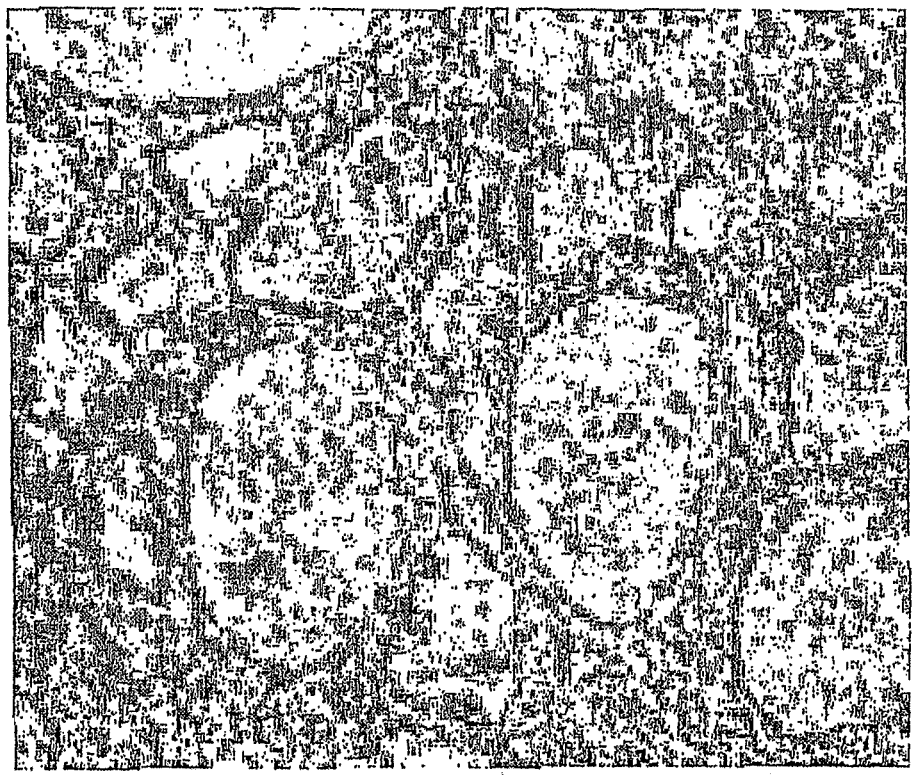
FIG. 3A. In vitro differentiation of RoSH2.1 cells on matrigel coated plate. In two weeks, RoSH2.1 cells differentiate to form a network of tubular structures that covered the surface of the entire tissue dish.
Figure 3B:
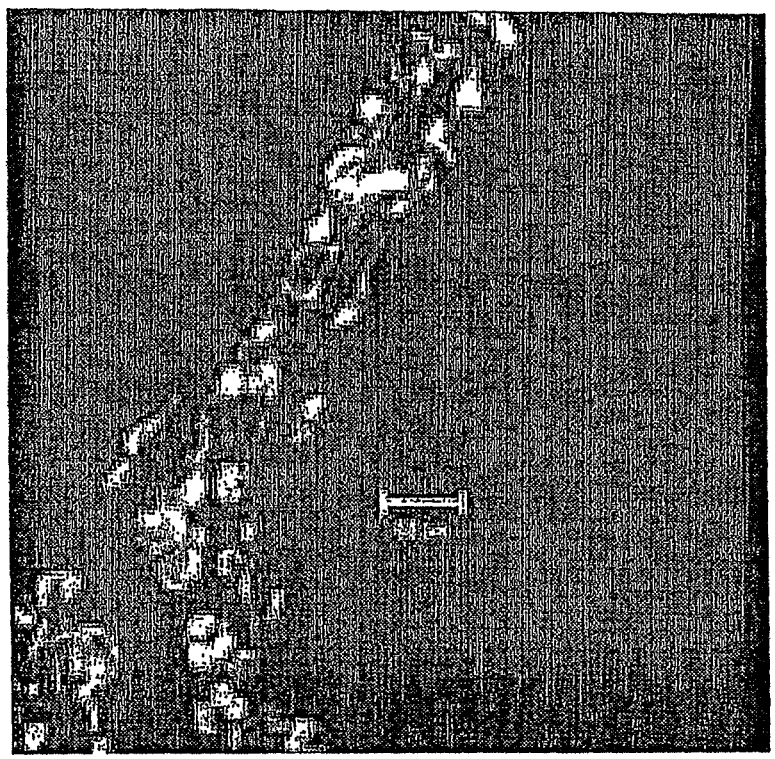
FIG. 3B. E-RoSH derived tubular structures have patent lumens and endocytosed acetylated LDL. The structures are labeled with CFDA, a cytoplasmic green fluorescent dye (Molecular Probe, Eugene, Oreg.) and propidium iodide, and viewed by confocal microscopy (left panel). The tubular structures are incubated with acetylated red fluorescent diI-labelled LDL (Molecular Probe, Eugene, Oreg.) for 24 hours and counterstained with SYTOX Green™, a green fluorescent nuclear dye (Molecular Probe, Eugene, Oreg.) before analysis by confocal microscopy.
Figure 3B:
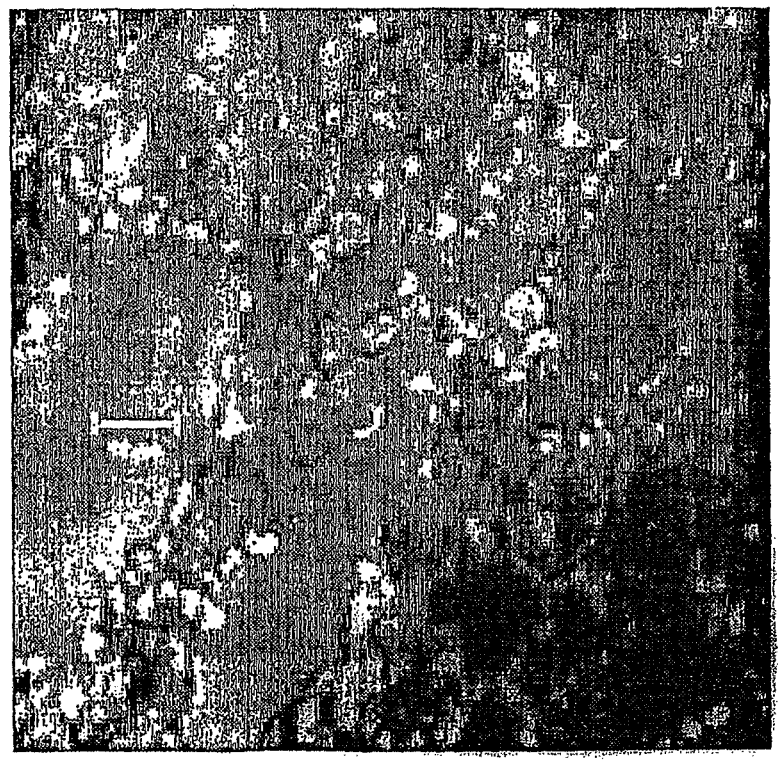
Figure 3C:
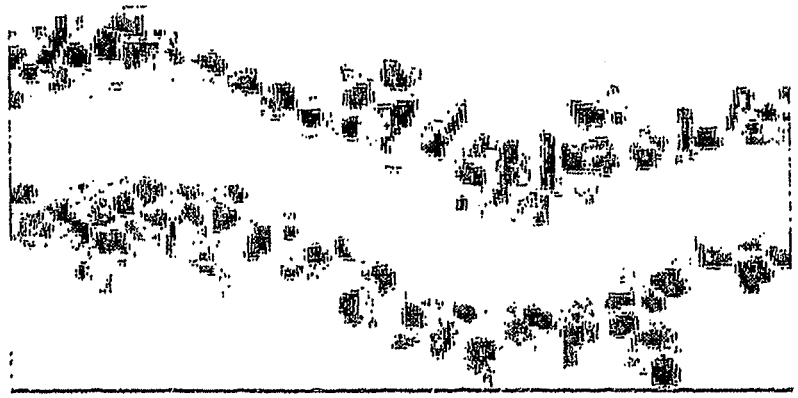
FIG. 3C. Immunoreactivity for vWF on paraffin-embedded sections of E-RoSH2.1 derived tubular structures are using HRP-based detection system. Brown precipitates indicate positive staining. The nuclei are stained with Mayer's hematoxylin.
Figure 3C:
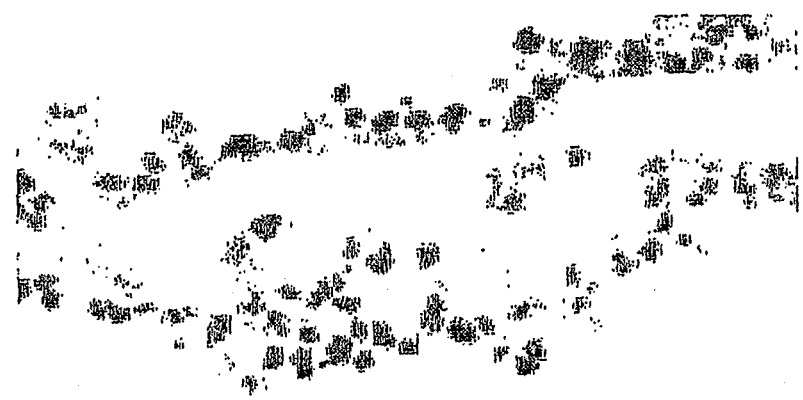

Within two weeks, the cells formed a network of vascular-like tubules that covered the entire tissue culture dish (FIG. 3A). These tubules are patent and cells lining the lumen endocytosed acetylated LDL (FIG. 3B) and are immunoreactive for vWF (FIG. 3C).

Figure 3D:
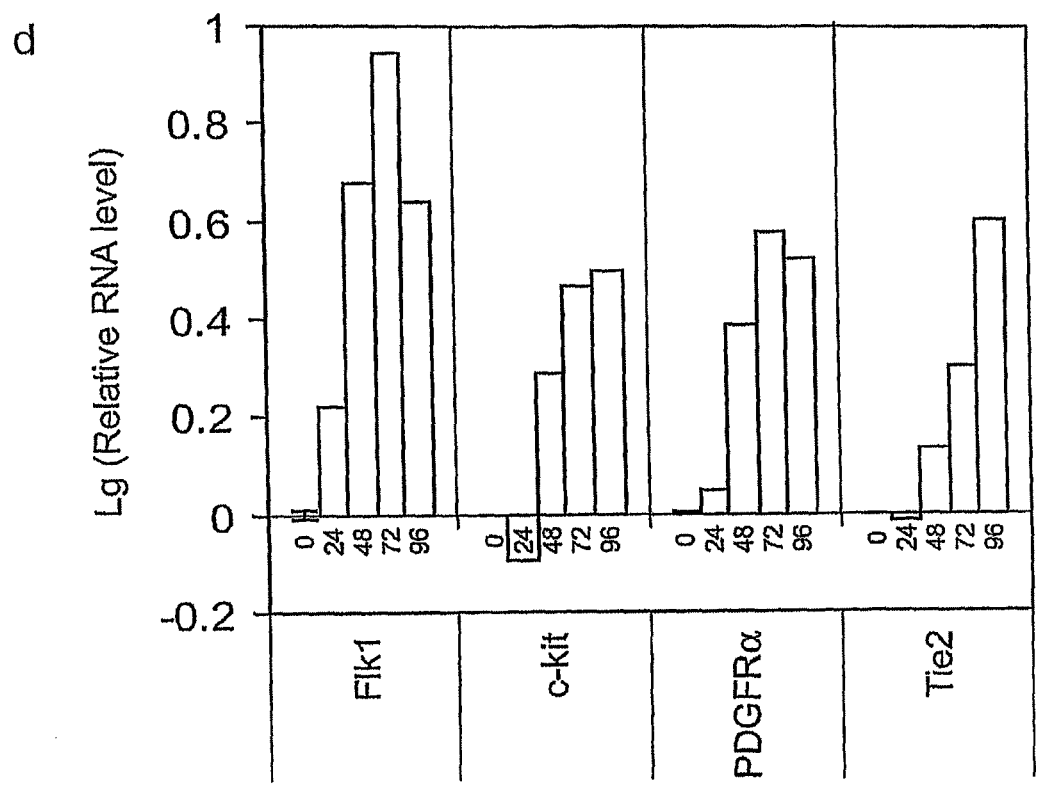
FIG. 3D. Gene expression during endothelial differentiation of E-RoSH2.1 cells as measured by quantitative RT-PCR analysis. Relative gene expression is normalized against that at time 0 and expressed as a logarithmic function.

Expression of endothelial genes such as Tie-2 is also increased (FIG. 3D).

Figure 3E:
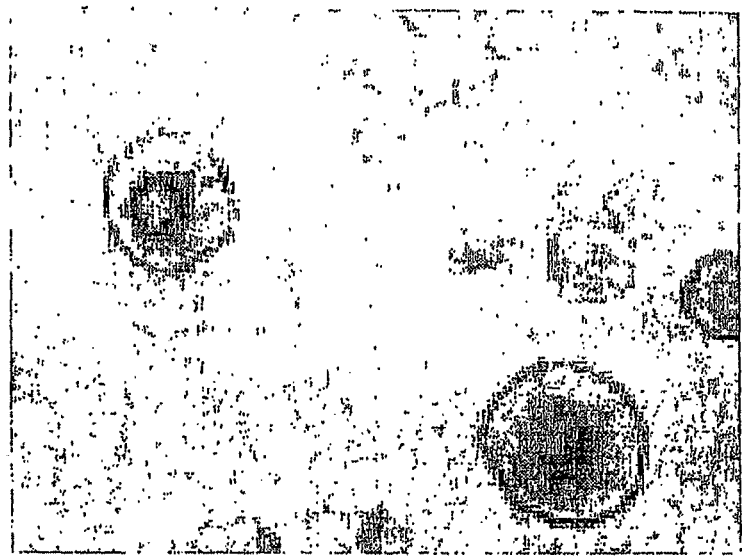
FIG. 3E. Suspension cultures of embryonic stem cells and E-RoSH at day 7
Figure 3E:
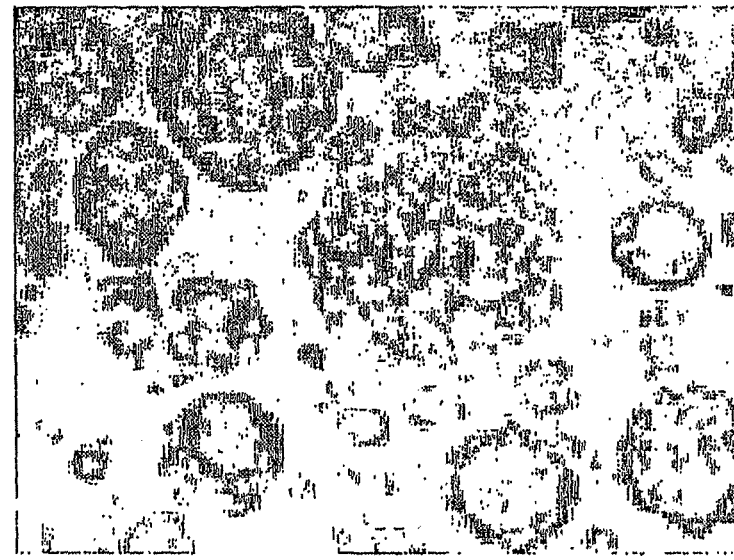

When grown in suspension, E-RoSH cells, like embryonic stem cells, formed spherical bodies. However, unlike the tightly packed embryonic stem cell-derived embryoid bodies, E-RoSH-derived bodies are morphologically distinct with a hollow center (FIG. 3E), providing another distinguishing difference between embryonic stem cells and E-RoSH cells.

Figure 3F:
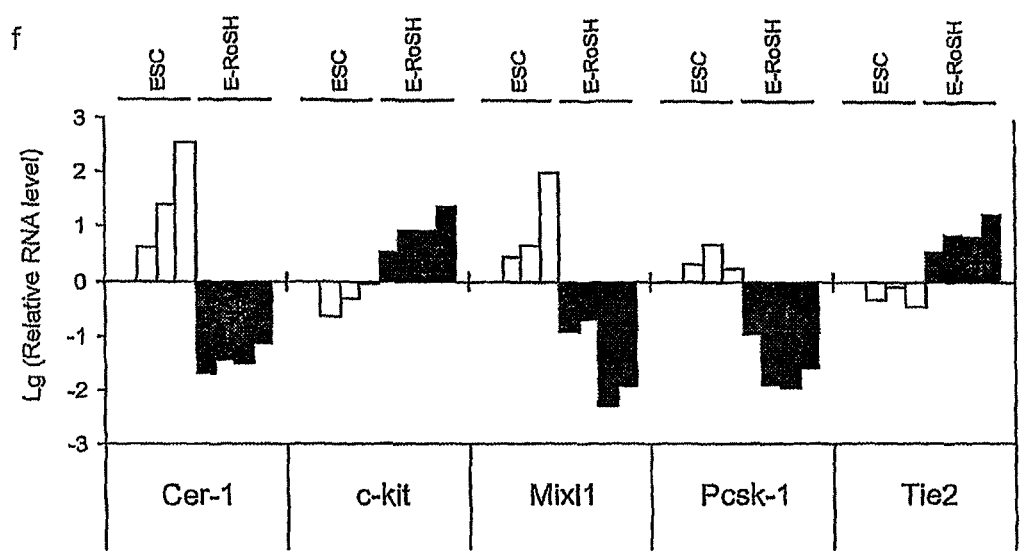
FIG. 3F. Quantitative RT-PCR profiling of gene expression by embryonic stem cells and E-RoSH2.1 cells when cultured in suspension cultures for 0, 2, 3 and 7 days. Relative gene expression is normalized against that of embryonic stem cells at time 0 and expressed as a logarithmic function.

Genes whose expressions are associated with early lineage commitment during embryonic development, are significantly reduced during formation of E-RoSH-derived bodies in comparison to that during embryoid body formation. These genes include cerberus (cer-1) which is expressed during early gastrulation (De Robertis et al, Int J Dev Biol. 2001; 45:189-197), mixl1 which is important for axial mesendoderm morphogenesis and patterning (Hart et al, Development. 2002; 129:3597-3608; Mohn et al, Dev Dyn. 2003; 226:446-459) and PCSK1 which is expressed in neuroendocrine tissues (Seidah et al, Mol Endocrinol. 1991; 5:111-122; Benjannet et al, Proc Natl Acad Sci USA. 1991; 88:3564-3568) (FIG. 3F).

The relatively low expression levels of these genes are consistent with the reduced potency of E-RoSH, and suggest that E-RoSH cells no longer have the capacity of embryonic stem cells to differentiate into a wide repertoire of cell types from all three germ layers.

In contrast, a ten-fold increase in the expression of endothelial genes such as c-kit and Tie-2 (FIG. 3F), suggests that E-RoSH cells preferentially differentiate into endothelial cells with a ten-fold efficiency over its parental embryonic stem cells. Although the gene expression of E-RoSH cells suggested that they have the potential to differentiate into hematopoietic cells, we have not been able to induce robust hematopoietic differentiation of these cells using standard hematopoietic differentiation assays.

Figure 3G:
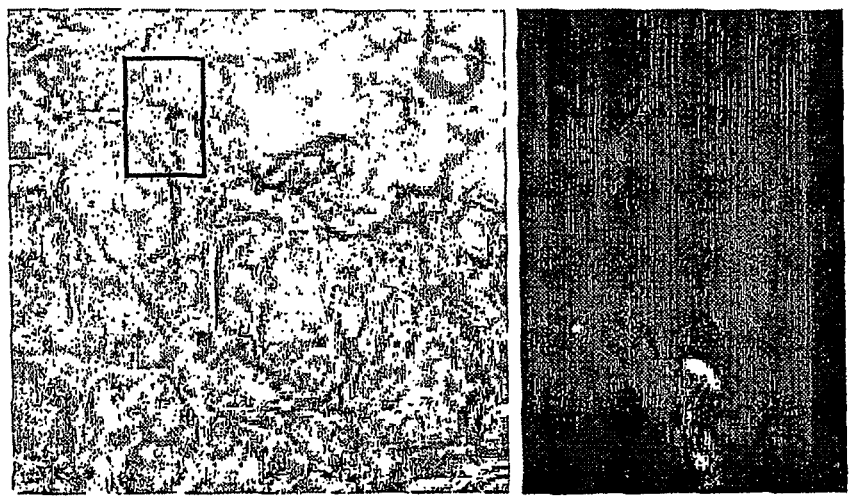
FIG. 3G. In vivo differentiation. $1 \times 10^5$ E-RoSH cells labeled with Qdot® nanocrystals (655 nm emission) are injected into a embryonic stem cell-derived teratoma that is induced in SCID mice. Three days later, the mice are euthanized and the tumors are removed. The tumors are fixed in 4% paraformaldehyde and cryosectioned at 20 μm thickness. The sections are assayed for pecam-1 immunoreactivity using rat anit-pecam1 followed by FITC-conjugated rabbit anti-rat antibody, and counterstained with DAPI. The sections are viewed by light microscopy and then confocal microscopy.

When E-RoSH cells are labeled with Q-tracker, a long term, cell-permeable fluorescent cell label, and transplanted into a parental embryonic stem cell-derived teratoma that will provide a suitable microenvironment for differentiating E-RoSH cells, E-RoSH cells are found to be incorporated into the capillary plexus in the teratoma and are immunoreactive for pecam-1 (FIG. 3G). Many of the transplanted cells that are not incorporated in the tumor vasculature are not immunoreactive for pecam-1 (data not shown).

Example 9

Derivation of Lineage-Restricted Progenitor Cell Lines from Human Embryonic Stem (hES) Cell Lines To illustrate the general applicability of our approach, we derived MSC-like lines from huES9 a human embryonic stem cells line (Cowan et al, N Engl J Med. 2004; 350:1353-1356).

Figure 4A:
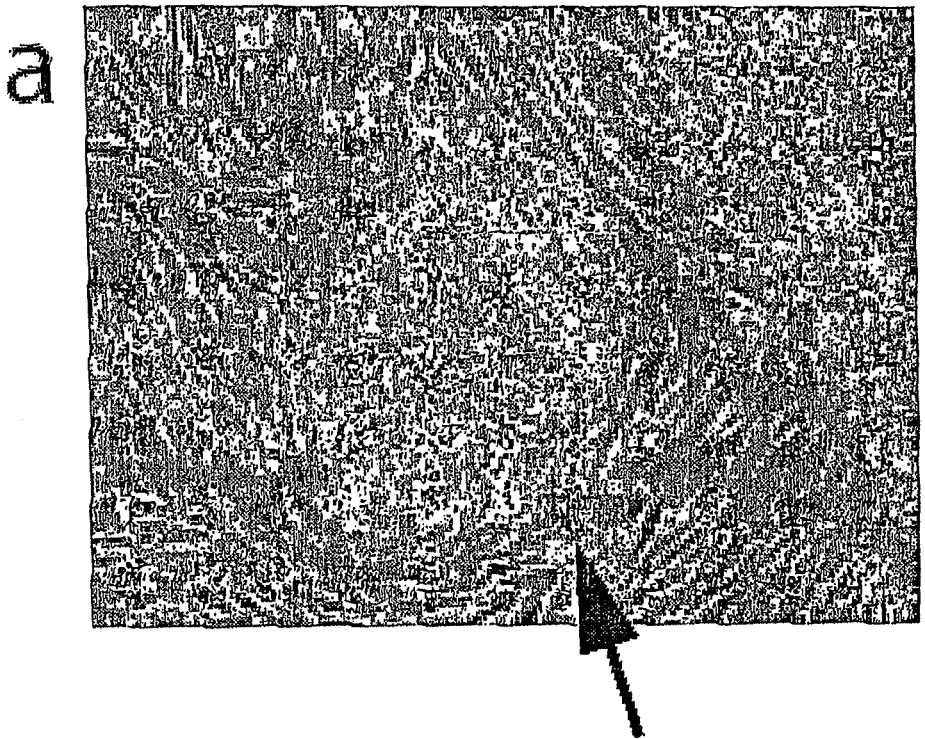
FIG. 4A. HuES9 colony grown on mitotically inactive MEFs surrounded by proliferating fibrobastic stromal cells (arrow).
Figure 4B:
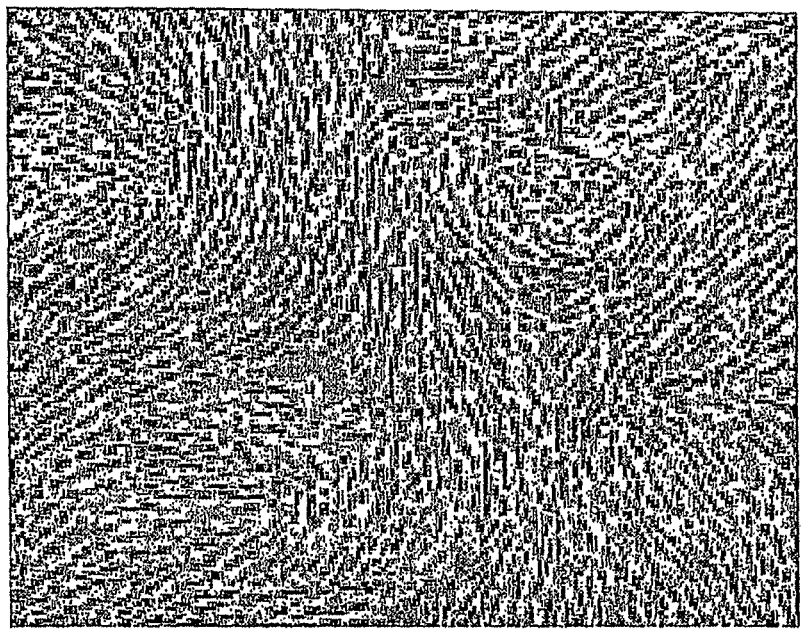
FIG. 4B. A representative confluent culture of HuES9.E1 MSC-like cells and BM-derived MSCs.
Figure 4B:
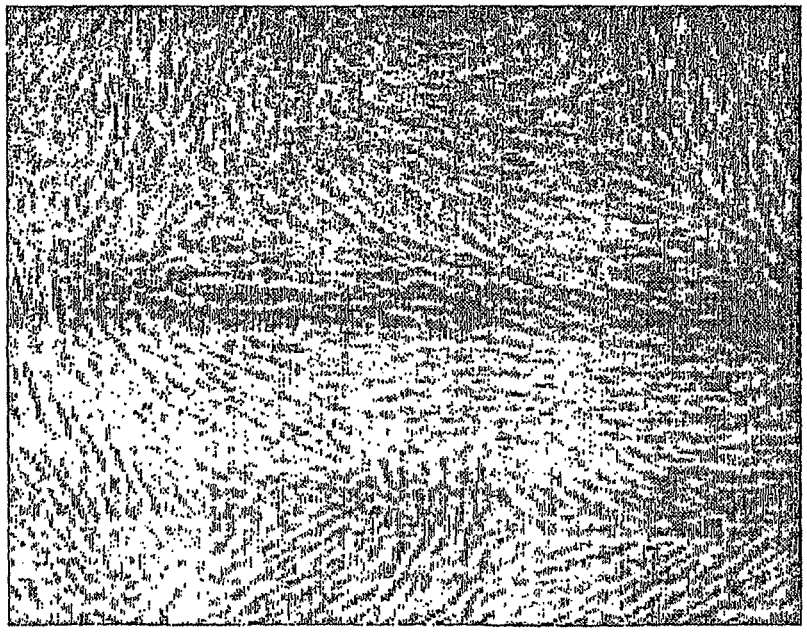

We observed that in most human embryonic stem cell cultures, human embryonic stem cell colonies grow in a state of equilibrium with proliferating stromal fibroblastic cells (FIG. 4A) suggesting that they are human embryonic stem cell-derived progenitor cells. To encourage the propagation of these cells and discourage that of human embryonic stem cells, huES9 cells are cultured and passaged in the absence of feeder. A homogenous culture of fibroblast-like cells that are morphologically similar to bone marrow derived MSC (BM MSC) cultures is generated (FIG. 4B).

Figure 4C:
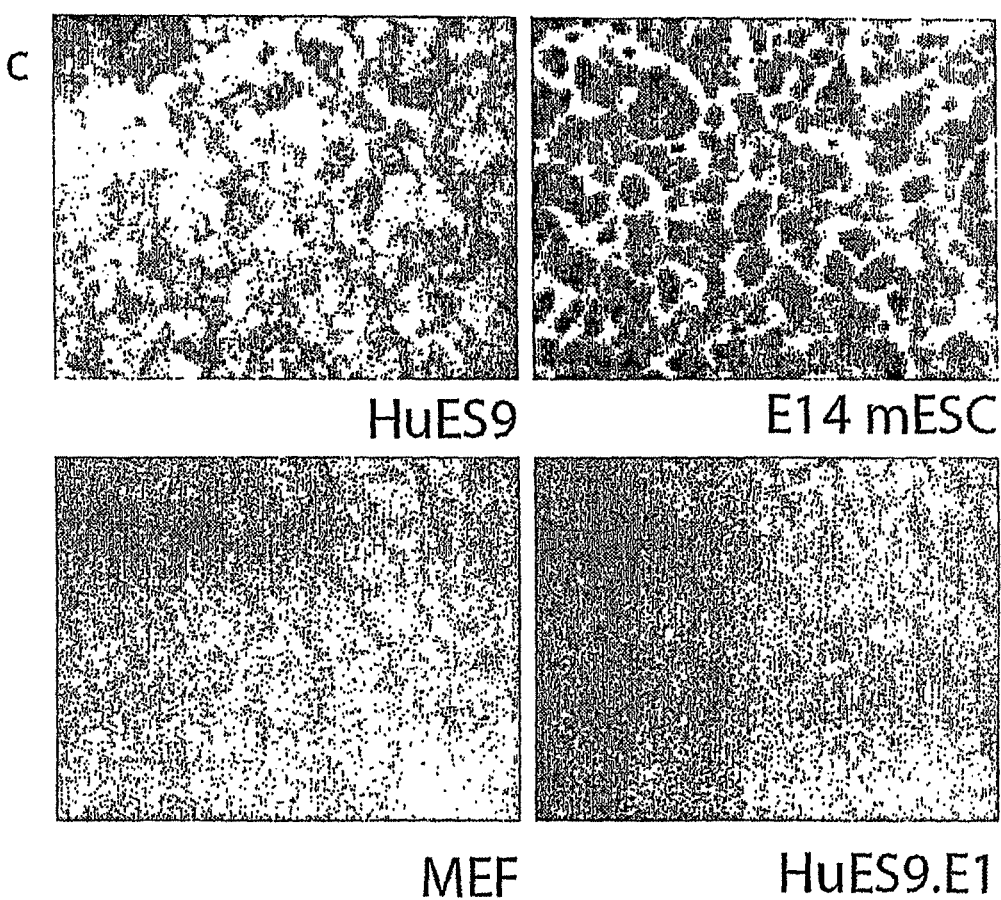
FIG. 4C. HuES9, a human embryonic stem cell line, E14, a mouse embryonic stem cell line, mouse embryonic fibroblast (MEF) and HuES9.E1 mesenchymal stem cell (MSC)-like cells are stained for the presence of alkaline phosphatase activity.
Figure 4D:
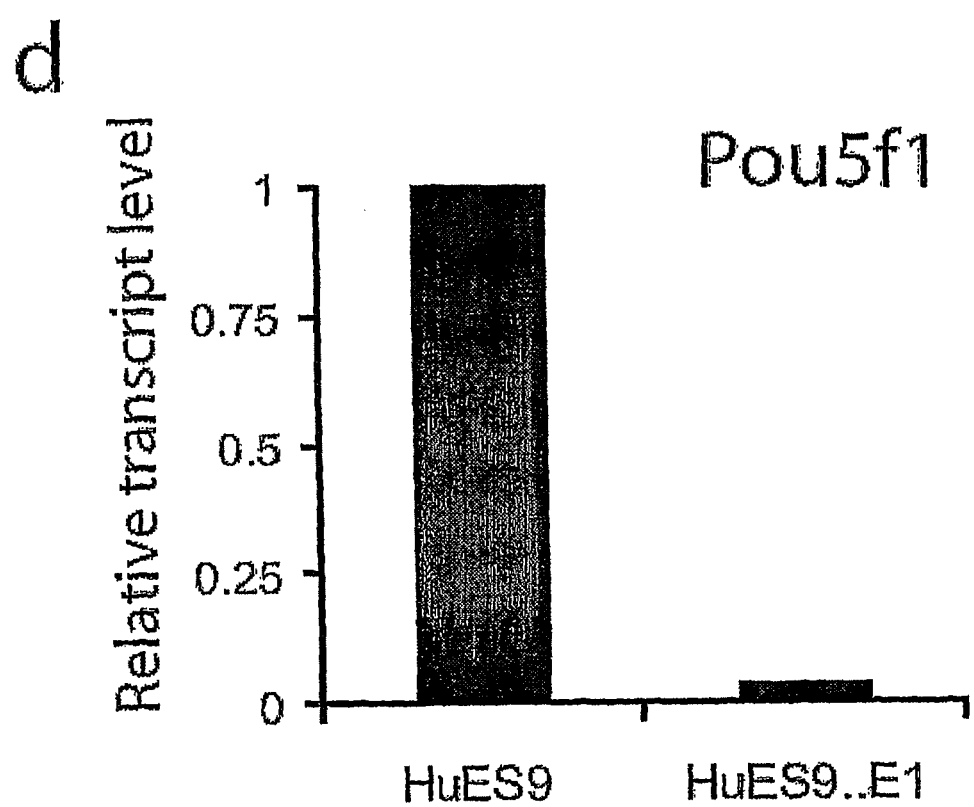
FIG. 4D. HuES9 and HuES9.E1 MSC-like cells are tested for the expression of Pou5f1 by quantitative RT-PCR analysis using TaqMan® primers. Pou5f1 transcript level in HuES9 human embryonic stem cell normalized to one.

Two polyclonal lines, named huES9.E1 and huES9.E3, are independently generated. Unlike its parental huES9 cells, huES9.E1 did not have detectable alkaline phosphatase activity (FIG. 4C) or express OCT4 (FIG. 4D).

Figure 4E:
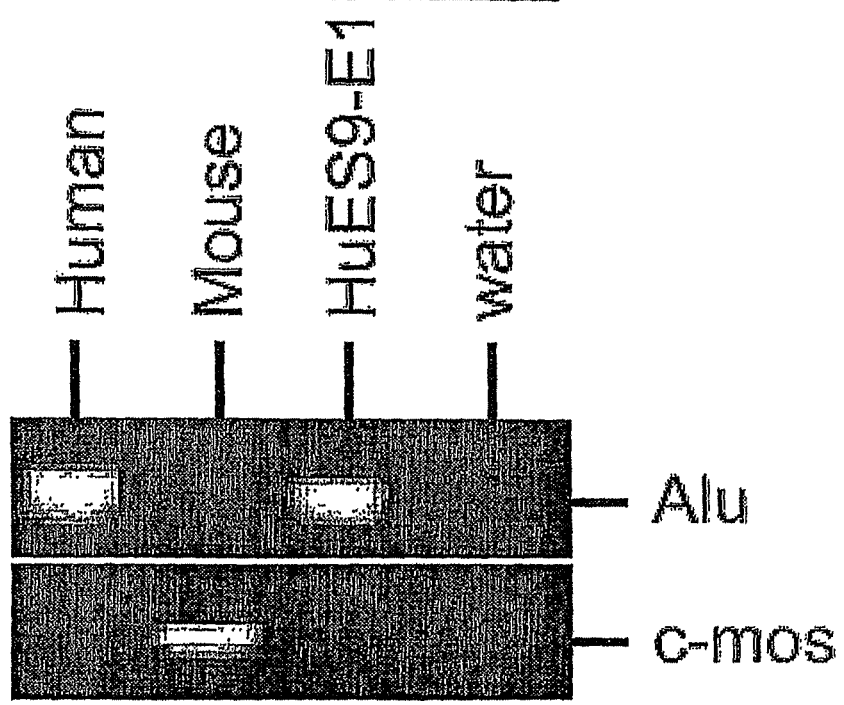
FIG. 4E. Genomic PCR analysis for the presence of human-specific Alu repeat sequence and mouse-specific c-mos repeat sequences in HuES9.E1 MSC-like cells.

As our previous experience suggests that fusion between putative stem cell and feeder cell occurs to generate self-renewing cells (Que et al, In Vitro Cell Dev Biol Anim. 2004; 40:143-149), these cultures are tested and shown to be negative for mouse-specific c-mos repeat sequences but positive for human specific alu repeat sequences (FIG. 4E).

The cells have 46, XX, chromosomes like its parental huES9 line (Cowan et al, N Engl J Med. 2004; 350:1353-1356) (FIG. 4F).

When grown in media supplemented with serum replacement media, the population doubling time is 4-5 days, and in media supplemented with 10% fetal calf serum, the population doubling is about 36 hours.

Based on the close resemblance of huES9.E1 and huES9.E3 to BM-MSC, we further approximated the lineage potential of huES9.E1 by comparing its surface antigen profile to that of BM-MSCs. These cells exhibited typical MSC surface markers, CD29+, CD44+, CD105+ and CD166+ (Barry and Murphy, Int J Biochem Cell Biol. 2004; 36:568-584) and did not express CD34 and CD45 (FIG. 4F).

Figure 4G:
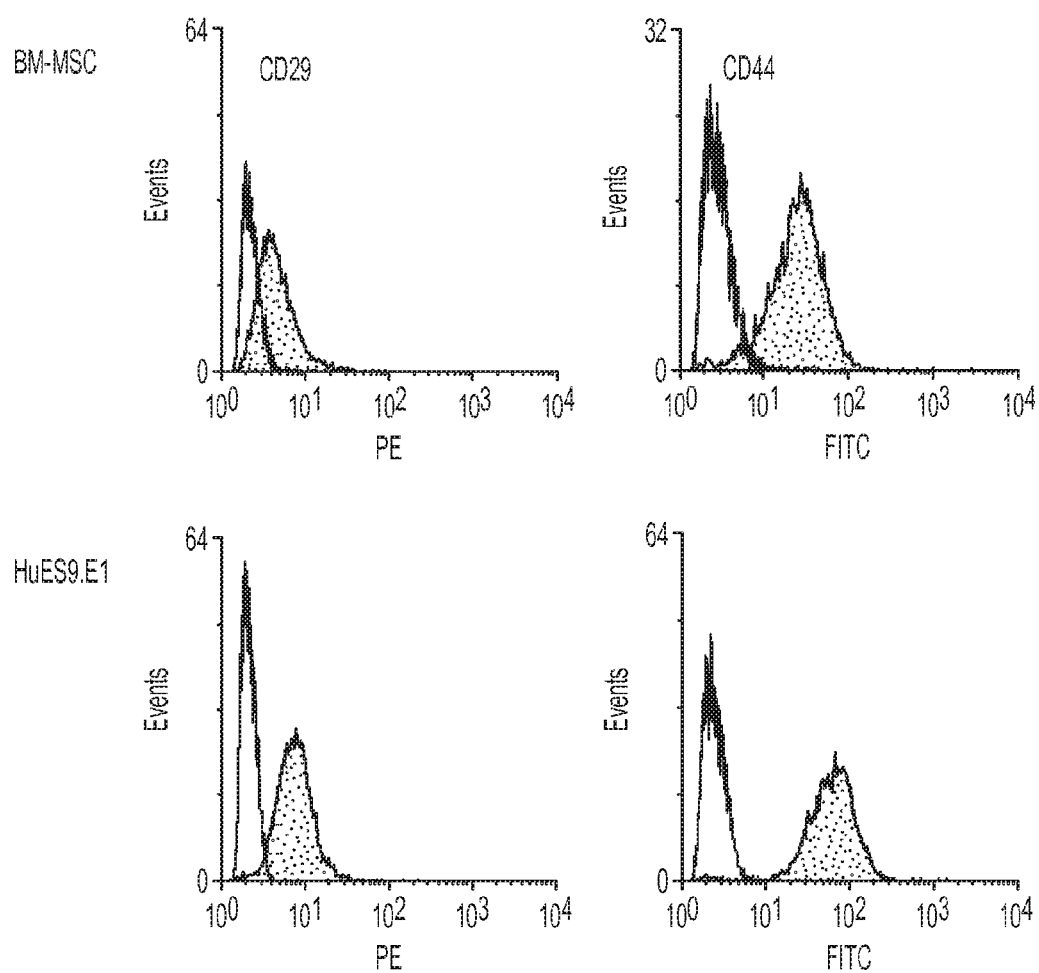
FIG. 4G. Profile of surface antigens by FACS analysis. HuES9.E1 cells are tested for immunoreactivity against CD29, CD44, CD105, CD166, CD34 and CD45.
Figure 4G:
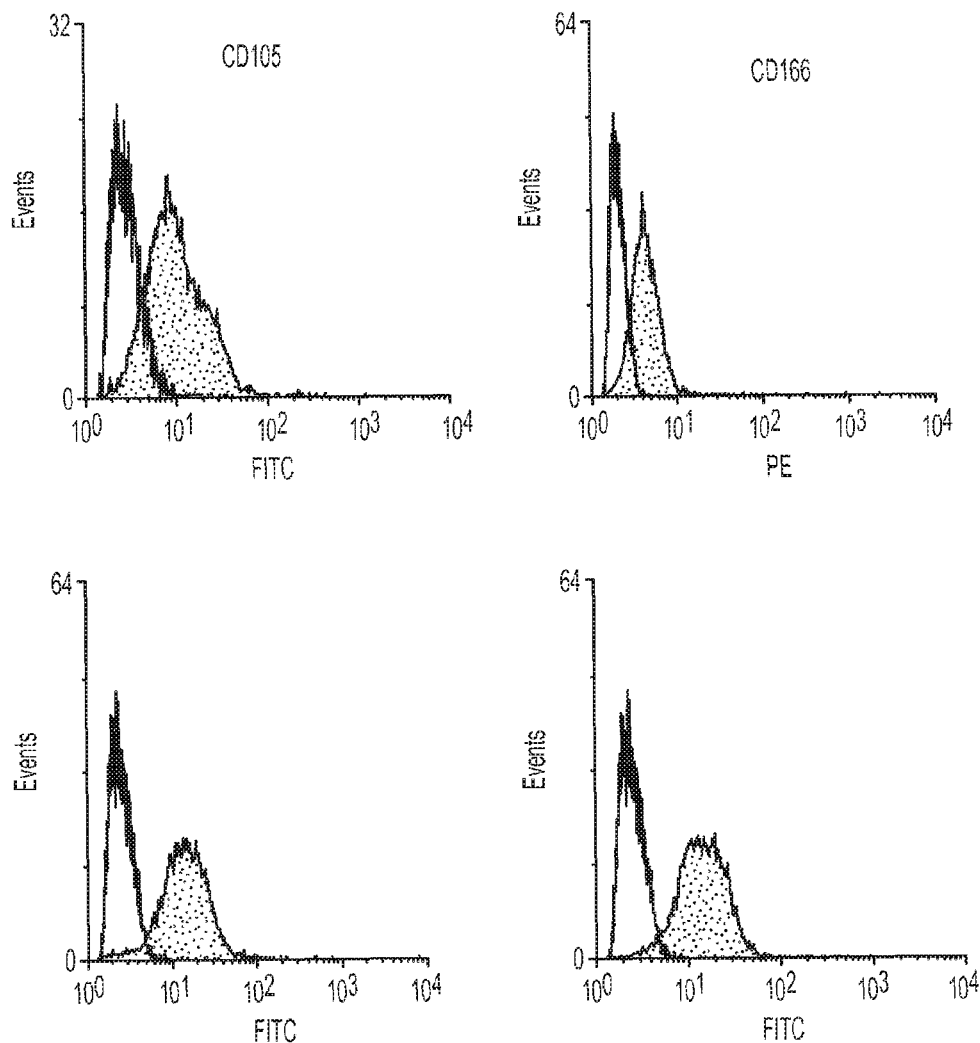
Figure 4G:
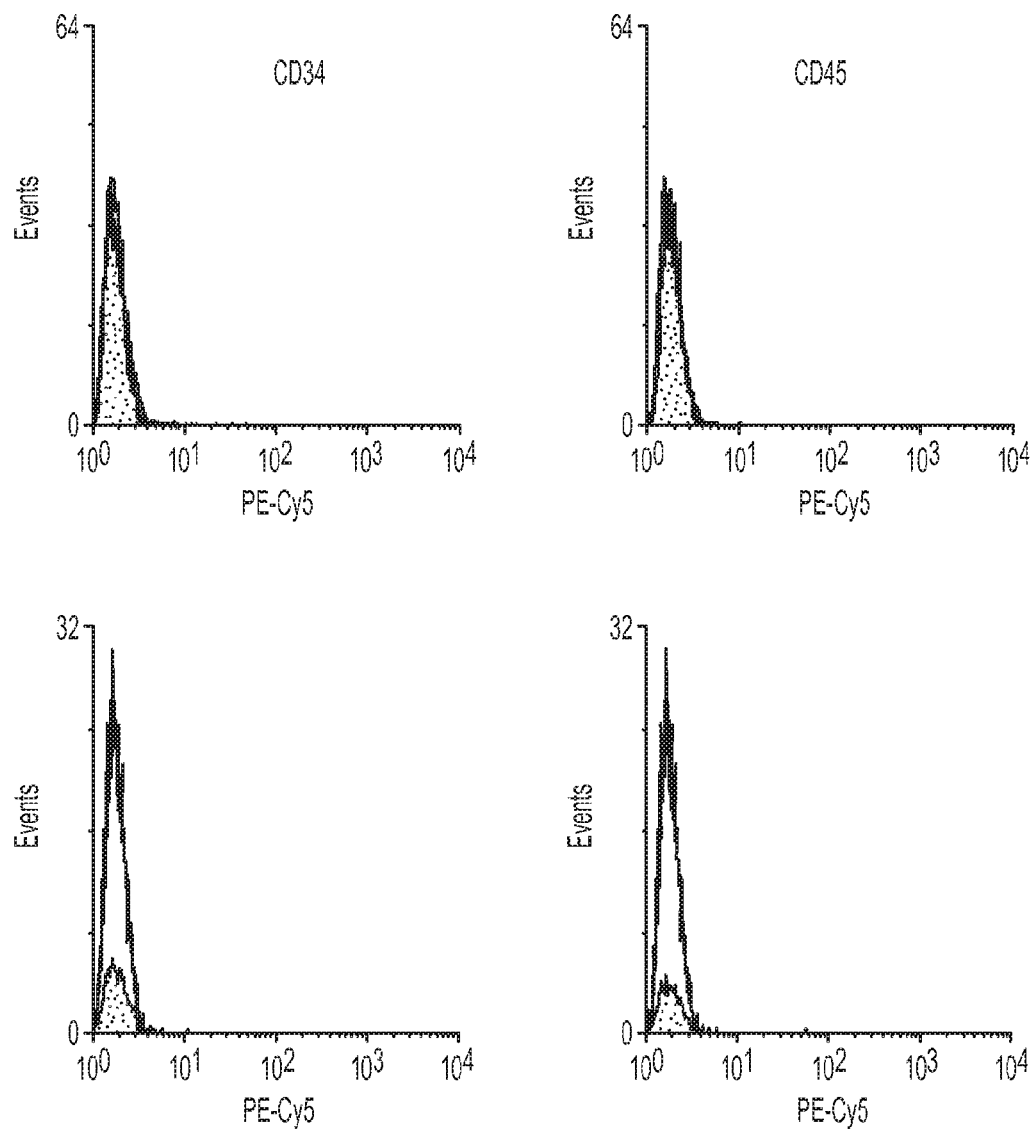
Figure 4H:
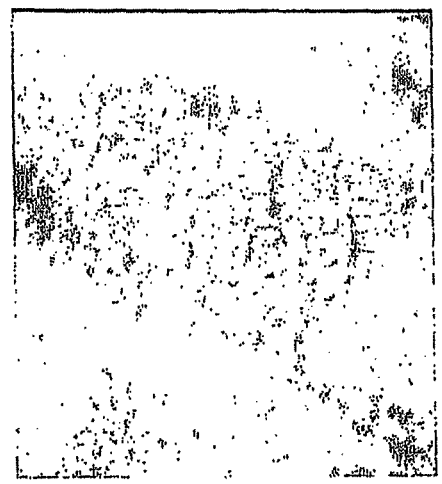
FIG. 4H. Differentiation of HuES9.E1 into adipocytes and osteocytes. Confluent HuES9.E1 cells are cultured in standard culture media for inducing adiogenesis or osteogenesis. After 12 days, cells that are induced to undergo adiogenesis are stained for oil droplets by oil red and analyzed for the expression of PPARγ by quantitative RT-PCR (top panel) while those that are induced to undergo osteogenesis are stained for calcium deposits by von Kossa staining and analyzed for the expression of bone-specific alkaline phosphatase, ALP by quantitative RT-PCR (bottom panel).
Figure 4H:
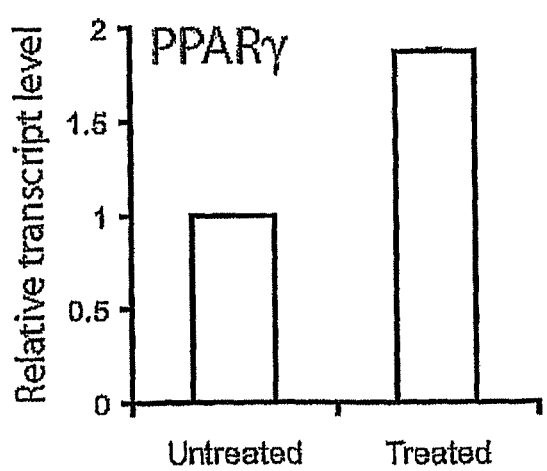
Figure 4H:
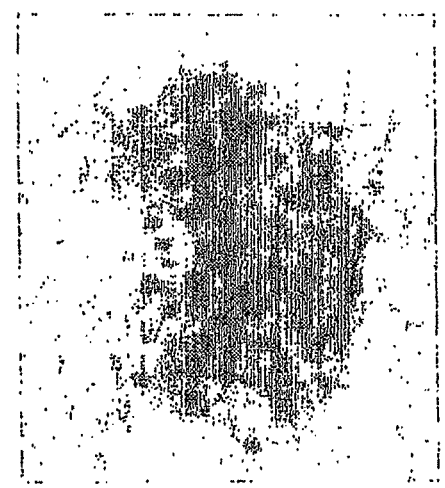
Figure 4H:
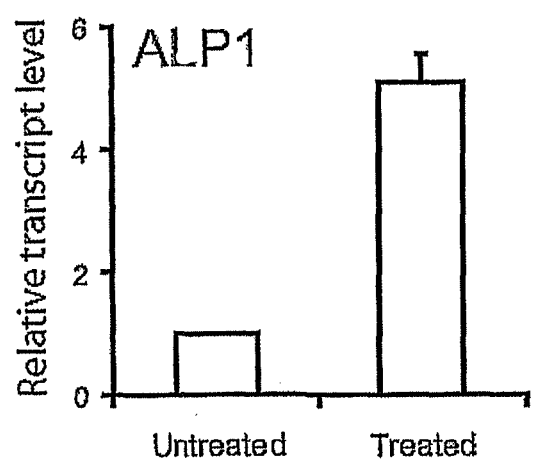

HuES9.E1 cells can be induced to differentiate into adipocytes and osteocytes using standard differentiation conditions (Barberi T et al, PLoS Med. 2005; 2:e161). Adipocytic differentiation is confirmed by the presence of oil droplets in the differentiated cells and expression of PPARγ mRNA (FIG. 4G) while osteogenesis is determined by von Kossa staining for calcium deposits in the matrix and expression of bone-specific alkaline phosphatase, Alp1 (FIG. 4H).

Example 9

Discussion

In summary, our study provides proof that lineage-restricted embryonic stem cell-derived progenitor cell lines can be established using the principle that progenitor cells with their unique ability to self-renew, can be propagated without transformation. They can be distinguished from terminally differentiating cells by their steady rate of proliferation without senescence.

Based on this distinguishing feature, these progenitor cells can be isolated by plating the differentiating cultures at low density to select for steadily proliferating colonies or by continual passaging of the culture to select for proliferating cells while terminally differentiating cells will senesce and will be lost from the cultures. One requirement is that the culture media does not promote propagation of the parental embryonic stem cells.

REFERENCES

1. Keller G. Embryonic stem cell differentiation: emergence of a new era in biology and medicine. Genes Dev. 2005; 19:1129-1155
2. Wobus A M, Boheler K R. Embryonic stem cells: prospects for developmental biology and cell therapy. Physiol Rev. 2005; 85:635-678
3. Wiles M V. Embryonic stem cell differentiation in Vitro. Methods in Enzymology. 1993; 225:900-918
4. Choi K, Chung Y S, Zhang W J. Hematopoietic and endothelial development of mouse embryonic stem cells in culture. Methods Mol Med. 2005; 105:359-368
5. Yin Y, Que J, Teh M, Cao W P, El Oakley R M, Lim S-K. Embryonic Cell Lines with Endothelial Potential: An In Vitro System for Studying Endothelial Differentiation. Arterioscler Thromb Vase Biol. 2004; 24:691-696
6. Lim S K, Bieker J J, Lin C S, Costantini F. A shortened life span of EKLF−/− adult erythrocytes, due to a deficiency of beta-globin chains, is ameliorated by human gamma-globin chains. Blood. 1997; 90:1291-1299
7. Bourc'his D, Xu G L, Lin C S, Bollman B, Bestor T H. Dnmt3L and the establishment of maternal genomic imprints. Science. 2001; 294:2536-2539

8. Wei C L, Miura T, Robson P, Lim S K, Xu X Q, Lee M Y, Gupta 5, Stanton L, Luo Y, Schmitt J, Thies S, Wang W, Khrebtukova I, Zhou D, Liu E T, Ruan Y J, Rao M, Lira B. Transcriptome profiling of human and murine ESCs identifies divergent paths required to maintain the stem cell state. Stem Cells. 2005; 23:166-185
9. Rao M. Conserved and divergent paths that regulate self-renewal in mouse and human embryonic stem cells. Dev Biol. 2004; 275:269-286
10. Jaffredo T, Bollerot K, Sugiyama D, Gautier R, Drevon C. Tracing the hemangioblast during embryogenesis: developmental relationships between endothelial and hematopoietic cells. Int J Dev Biol. 2005; 49:269-277
11. De Robertis E M, Wessely O, Oelgeschlager M, Brizuela B, Pera E, Larrain J, Abreu J, Bachiller D. Molecular mechanisms of cell-cell signaling by the Spemann-Mangold organizer. Int J Dev Biol. 2001; 45:189-197
12. Hart A H, Hartley L, Sourris K, Stadler E S, Li R, Stanley E G, Tam P P, Elefanty A G, Robb L. Mixl1 is required for axial mesendoderm morphogenesis and patterning in the murine embryo. Development. 2002; 129:3597-3608
13. Mohn D, Chen S W, Dias D C, Weinstein D C, Dyer M A, Sahr K, Ducker C E, Zahradka E, Keller G, Zaret K S, Gudas L J, Baron M H. Mouse Mix gene is activated early during differentiation of ES and F9 stem cells and induces endoderm in frog embryos. Dev Dyn. 2003; 226:446-459
14. Seidah N G, Marcinkiewicz M, Benjannet S, Gaspar L, Beaubien G, Mattei M G, Lazure C, Mbikay M, Chretien M. Cloning and primary sequence of a mouse candidate prohormone convertase PC1 homologous to PC2, Furin, and Kex2: distinct chromosomal localization and messenger RNA distribution in brain and pituitary compared to PC2. Mol Endocrinol. 1991; 5:111-122
15. Benjannet S, Rondeau N, Day R, Chretien M, Seidah N G. PC1 and PC2 are proprotein convertases capable of cleaving proopiomelanocortin at distinct pairs of basic residues, Proc Natl Acad Sci USA, 1991; 88:3564-3568
16. Cowan C A, Klimanskaya I, McMahon J, Atienza 7, Witmyer 3, Zucker J P, Wang S, Morton C C, McMahon A P, Powers D, Melton D A. Derivation of embryonic stem-cell lines from human blastocysts. N Engl J Med. 2004; 350:1353-1356
17. Que 3, El Oakley R M, Salto-Tellez M, Wong N, de Kleijn D P, Teh M, Retnam L, Lim S K. Generation of hybrid cell lines with endothelial potential from spontaneous fusion of adult bone marrow cells with embryonic fibroblast feeder. In Vitro Cell Dev Biol Anim. 2004; 40:143-149
18. Barry F P, Murphy J M. Mesenchymal stem cells: clinical applications and biological characterization. Int J Biochem Cell Biol. 2004; 36:568-584
19. Barberi T, Willis L M, Socci N D, Studer L. Derivation of multipotent mesenchymal precursors from human embryonic stem cells. PLoS Med. 2005; 2:e161
20. Robertson E J. Embryo-derived stem cell lines. In: Robertson E J, ed. Teratocarcinomas and embryonic stem cells: a practical approach. Oxford: IRL Press Limited; 1987:71-112
21. Pittenger M F, Mackay A M, Beck S C, Jaiswal R K, Douglas R, Mosca J D, Moorman M A, Simonetti D W, Craig S, Marshals et a. Multilineage potential of adult human mesenchymal stem cells. Science. 1999; 284:143-147

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments and that many modifications and additions thereto may be made within the scope of the invention. Indeed, various modifications of the described modes for carrying out the invention which are obvious to those skilled in molecular biology or related fields are intended to be within the scope of the claims. Furthermore, various combinations of the features of the following dependent claims can be made with the features of the independent claims without departing from the scope of the present invention.

We claim:

1. A method of screening a candidate molecule for its effect on a human mesenchymal progenitor cell, the method comprising:
    (a) providing a parental embryonic stem cell or descendants of a parental embryonic stem cell obtained by dispersing an embryonic stem cell colony with trypsin, wherein the parental embryonic stem cell is a human embryonic stem cell; and
    (b) culturing the parental embryonic stem cell in the absence of feeder cells in rich media comprising (i) essential nutrients required for cell growth and (ii) serum or serum replacement, wherein the rich media does not comprise additional grown regulators or hormones that promote growth of embryonic stem cells, and wherein the culturing produces mesenchymal progenitor cells which self renew;
    thereby establishing in the absence of transformation a mesenchymal progenitor cell line from the mesenchymal progenitor cells which self-renew; wherein the mesenchymal progenitor cell line is maintainable in cell culture for more than 20 generations, and wherein the mesenchymal progenitor cell line is lineage restricted compared to the parental embryonic stem cell;
    (c) culturing cells from the mesenchymal progenitor cell line in the presence of a candidate molecule; and
    (d) determining the effect of a candidate molecule on cells from the mesenchymal progenitor cell line treated with the candidate molecule compared with untreated cells from the mesenchymal progenitor cell line or cells from the mesenchymal progenitor cell line treated with an inert compound.

2. The method according to claim 1, wherein the mesenchymal progenitor cell line is maintainable in cell culture for more than 25 generations.

3. The method according to claim 1, wherein the mesenchymal progenitor cell line is maintainable in cell culture for more than 30 generations.

4. The method according to claim 1, wherein the mesenchymal progenitor cell line is maintainable in cell culture for more than 35 generations.

5. The method according to claim 1, wherein the mesenchymal progenitor cell line is maintainable in cell culture for more than 40 generations.

6. A method of screening a candidate molecule for its effect on a cell differentiated from a human mesenchymal progenitor cell line, the method comprising:
    (a) providing a parental embryonic stem cell or descendants of a parental embryonic stem cell obtained by dispersing an embryonic stem cell colony with trypsin, wherein the parental embryonic stem cell is a human embryonic stem cell; and (b) culturing the parental embryonic stem cell in the absence of feeder cells in rich media comprising (i) essential nutrients required for cell growth and (ii) serum or serum replacement, wherein the rich media does not comprise additional grown regulators or hormones that promote growth of embryonic stem cells, and wherein the culturing produces mesenchymal progenitor cells which self-renew;

thereby establishing in the absence of transformation a mesenchymal progenitor cell line from the mesenchymal progenitor cells which self-renew; wherein the mesenchymal progenitor cell line is maintainable in cell culture for more than 20 generations, and wherein the mesenchymal progenitor cell line is lineage restricted compared to the parental embryonic stem cell;

(c) deriving a differentiated cell from the mesenchymal progenitor cell line;

(d) treating the differentiated cell with a candidate molecule; and (e) determining the effect of a candidate molecule on the differentiated cell treated with the candidate molecule compared with untreated differentiated cells or differentiated cells treated with an inert compound.

7. The method according to claim 6, wherein the mesenchymal progenitor cell line is maintainable in cell culture for more than 25 generations.

8. The method according to claim 6, wherein the mesenchymal progenitor cell line is maintainable in cell culture for more than 30 generations.

9. The method according to claim 6, wherein the mesenchymal progenitor cell line is maintainable in cell culture for more than 35 generations.

10. The method according to claim 6, wherein the mesenchymal progenitor cell line is maintainable in cell culture for more than 40 generations.

11. The method according to claim 1, wherein the rich media is DMEM with D-glucose, fetal calf serum, non-essential amino acids, L-glutamine, and β-mercaptoethanol.

12. The method according to claim 6, wherein the rich media is DMEM with D-glucose, fetal calf serum, non-essential amino acids, L-glutamine, and β-mercaptoethanol.

13. The method according to claim 1, wherein the mesenchymal progenitor cells which self-renew are $CD29^+$, $CD44^+$, $CD105^+$, $CD166^+$, $CD34^-$, and $CD45^-$.

14. The method according to claim 6, wherein the mesenchymal progenitor cells which self-renew are $CD29^+$, $CD44^+$, $CD105^+$, $CD166^+$, $CD34^-$, and $CD45^-$.

* * * * *